(12) United States Patent
Hinnah et al.

(10) Patent No.: US 8,580,577 B2
(45) Date of Patent: Nov. 12, 2013

(54) METHOD FOR DETECTING AN ANALYTE IN A SAMPLE

(75) Inventors: Silke Hinnah, Hamburg (DE); Dagmar Lambrü, Faßberg (DE); Sonja Dröge, Elmshorn (DE); Stefan Jäger, Hamburg (DE); Karsten Gall, Lunestedt (DE); Werner Stürmer, Wahlwies (DE); Michaela Schäfer, Orsingen-Nenzingen (DE)

(73) Assignee: Evotec AG, Hamburg (DE)

( * ) Notice: Subject to any disclaimer, the term of this patent is extended or adjusted under 35 U.S.C. 154(b) by 490 days.

(21) Appl. No.: 12/662,896

(22) Filed: May 10, 2010

(65) Prior Publication Data

US 2011/0105348 A1 May 5, 2011

Related U.S. Application Data

(63) Continuation of application No. 10/539,628, filed as application No. PCT/EP03/14661 on Dec. 19, 2003, now abandoned.

(60) Provisional application No. 60/439,439, filed on Jan. 13, 2003.

(30) Foreign Application Priority Data

Dec. 20, 2002 (EP) ..................................... 02028582

(51) Int. Cl.
| | |
|---|---|
| *G01N 33/566* | (2006.01) |
| *G01N 33/53* | (2006.01) |
| *G01N 33/543* | (2006.01) |
| *G01N 33/554* | (2006.01) |
| *G01N 21/00* | (2006.01) |
| *G01N 21/76* | (2006.01) |
| *C12Q 1/68* | (2006.01) |

(52) U.S. Cl.
USPC .............. 436/501; 435/6.1; 435/7.1; 436/518; 436/519; 436/164; 436/172

(58) Field of Classification Search
None
See application file for complete search history.

(56) References Cited

U.S. PATENT DOCUMENTS

| | | |
|---|---|---|
| 5,784,162 A | 7/1998 | Cabib et al. |
| 6,218,132 B1 | 4/2001 | Spack et al. |

(Continued)

FOREIGN PATENT DOCUMENTS

| | | |
|---|---|---|
| WO | WO 90/01564 | 2/1990 |
| WO | WO 9513399 | 5/1995 |
| WO | WO 9513399 A1 | 5/1995 |

OTHER PUBLICATIONS

Nolan et al. A simple quenching method for fluorescence background reduction and its application to the direct, quantitative detection of specific mRNA. Anal. Chem. 75:6236-6243, Nov. 15, 2003.

(Continued)

*Primary Examiner* — Samuel Woolwine
(74) *Attorney, Agent, or Firm* — Jacobson Holman PLLC

(57) ABSTRACT

The present invention relates to a method for detecting an analyte in a sample comprising the steps of
  providing detection probes being labeled with a first reporter, which detection probes are capable of binding to the analyte,
  providing a solid support,
  providing capture probes being bound or capable of binding to the solid support, which capture probes are capable of binding to the analyte, thus concentrating the analyte on the solid support,
  contacting the sample with the detection probes, the solid support and the capture probes, and
  detecting the detection probes, wherein
    the detection of detection probes is conducted in the presence of quenching probes binding to surplus detection probes not being bound to the analyte and thereby quenching at least partially an emission of the first reporter of said surplus detection probes and/or
    the solid support is labeled with a second reporter different from the first reporter, imaging the sample at an emission wavelength of the second reporter, generating a mask obtained from imaging the sample at the emission wavelength of the second reporter and applying this mask to an image of the sample used for detecting the detection probes.

60 Claims, 12 Drawing Sheets

(56) References Cited

U.S. PATENT DOCUMENTS

| | | |
|---|---|---|
| 6,251,615 B1 | 6/2001 | Oberhardt |
| 6,495,324 B1 | 12/2002 | Mirkin et al. |
| 6,544,730 B1 | 4/2003 | Deininger et al. |
| 6,589,742 B2 | 7/2003 | Edman et al. |
| 7,202,036 B2 | 4/2007 | Cai et al. |
| 2002/0177235 A1 | 11/2002 | Mabile et al. |
| 2003/0082571 A1 | 5/2003 | Kachab et al. |
| 2003/0129296 A1 | 7/2003 | Kelso |
| 2003/0219151 A1 | 11/2003 | Curry et al. |
| 2004/0022777 A1 | 2/2004 | Kolb et al. |
| 2008/0213762 A1 | 9/2008 | Yamamoto |

OTHER PUBLICATIONS

Li et al. A new class of homogeneous nucleic acid probes based on specific displacement hybridization. Nucleic Acids Research 30(2) e5 (pp. 1-9), Jan. 15, 2002.

Urdea et al. A comparison of non-radioisotopic hybridization assay methods using fluorescent, chemiluminescent and enzyme labeled synthetic oligodeoxyribonucleotide probes. Nucleic Acids Research 16(11):4937-56 (1988).

Spiro, et al., "A Bead-Based Method for Multiplexed Identification and Quantitation of DNA Sequences Using Flow Cytometry," Applied and Environmental Microbiology, vol. 66, No. 10, Oct. 2000, p. 4258-4265, [XP001069133].

Nolan et al. "A simple quenching method for fluorescence background reduction and its application to the direct, quantitative detection of specific mRNA." Anal. Chem. 75:6236-6243, Nov. 15, 2003.

Li et al. "A new class of homogenous nucleic acid probes based on specific displacement hybridization." Nucleic Acids Research, 30(2) e5 (pp. 1-9), Jan. 15, 2002.

Urdea et al. "A comparision of non-radioisotopic hybridization assay methods using fluorescent, chemiluminescent and enzyme labeled synthetic oligodeoxyribonucleotide probes." Nucleic Acids Research 16(11): 4937-56 (1988).

METHOD FOR DETECTING AN ANALYTE IN A SAMPLE

This is a continuation of Ser. No. 10/539,628, filed, Jun. 17, 2005, which is a 371 of PCT/EP03/14661, filed Dec. 19, 2003, which claims the benefit of U.S. Provisional Application No. 60/439,439, filed Jan. 13, 2003.

The present invention pertains to a method for detecting an analyte in a sample utilizing probes interacting with the analytes.

The detection and preferably quantitative analysis of nucleic acids is an important tool in the molecular biology laboratory. Examples are genetic tests, virus diagnostics, and analysis of polymorphisms. To date a number of DNA/RNA quantification systems have been developed. Typically, such quantification systems rely on an amplification step being performed exponentially (realized by Polymerase chain reaction (PCR), which is based on a specific, multiple turnover replication of the nucleic acid section to be identified) or linearly (realized by enzymatic turnover). Many detection and quantification systems rely on detecting analytes by labeled probes added to the sample in surplus. A part of the labeled probes binds to the analytes. When the binding reaction is complete, the unbound labeled probed is washed away, and the amount of analyte is quantified by the amount of bound labeled probe. Typically such washing steps are indispensable to reduce the background signals stemming from unbound probes. However, washing steps are difficult to manage, if manageable at all, in an automated way. Automation, on the other hand, is a prerequisite for high throughput applications typical in mass diagnostics, drug testing and development and alike situations.

An object of the present invention is to provide a sensitive method for the detection of low concentrations of analytes, such as nucleic acids. The method should in particular be feasible (i) without additional amplification steps thereby allowing a direct detection of the analyte and (ii) in a homogeneous format without relying on washing or other separation steps.

In a first aspect, the object of the present invention is accomplished by a method for detecting an analyte in a sample comprising the steps of
providing detection probes being labeled with a first reporter, which detection probes are capable of binding to the analyte,
providing a solid support,
providing capture probes being bound or capable of binding to the solid support, which capture probes are capable of binding to the analyte, thus concentrating the analyte on the solid support,
contacting the sample with the detection probes, the solid support and the capture probes, and
detecting the detection probes, wherein
the detection of detection probes is conducted in the presence of quenching probes binding to surplus detection probes not being bound to the analyte and thereby quenching at least partially an emission of the first reporter of said surplus detection probes and/or
the solid support is labeled with a second reporter different from the first reporter, imaging the sample at an emission wavelength of the second reporter, generating a mask obtained from imaging the sample at the emission wavelength of the second reporter and applying this mask to an image of the sample used for detecting the detection probes.

In a second aspect, which is particularly suited for detecting nucleic acid analytes, the object of the present invention is accomplished by a method comprising the steps of
providing detection oligonucleotides being labeled with a first reporter, which detection oligonucleotides are capable of binding to the analyte,
providing a solid support,
providing capture oligonucleotides being bound or capable of binding to the solid support, which capture oligonucleotides are capable of binding to the analyte, thus concentrating the analyte on the solid support,
contacting the sample with the detection oligonucleotides, the solid support and the capture oligonucleotides, and
detecting the detection oligonucleotides, wherein
the detection of detection oligonucleotides is conducted in the presence of quenching oligonucleotides hybridizing to surplus detection oligonucleotides not being bound to the analyte and thereby quenching at least partially an emission of the first reporter of said surplus detection oligonucleotides and/or
the solid support is labeled with a second reporter different from the first reporter, imaging the sample at an emission wavelength of the second reporter, generating a mask obtained from imaging the sample at the emission wavelength of the second reporter and applying this mask to an image of the sample used for detecting the detection oligonucleotides.

It is understood that the above mentioned method steps of providing the detection probes/detection oligonucleotides, solid support and capture probes/capture oligonucleotides do not represent necessarily the sequential order.

The method of the invention is advantageous since no washing steps and no amplification of the signal is necessary. Consequently, in a preferred embodiment the method is indeed conducted in a homogeneous format. In the case of detecting nucleic acid analytes, a direct detection of the analytes by the use of detection oligonucleotides becomes possible. Furthermore, well established confocal detection systems and devices become applicable. The signal intensity of the first reporter labeling the detection probe bound to the analyte, which is e.g. fluorescent light, is directly linked to the amount of analytes, omitting any amplifying turnover step. Consequently, the present invention allows for a quantification of the analyte. This makes the method according to the present invention easy to handle, extremely robust and amenable to high throughput applications. Additional features are a dynamic range of 3 orders of magnitude, variability smaller than 15% and the feasibility to miniaturize the reaction volumes to about 25 µL, while reading and evaluating a 384 sample plate within about 10 minutes.

According to the invention it becomes possible to determine analytes such as proteins and nucleic acids. In particular, the analyte comprises at least two binding sites, one for the capture probe and another one for the detection probe.

It is preferred that the first and/or second reporter is luminescent, in particular fluorescent. In an additional embodiment, the first and/or second reporter is a dye. The detection probes, in particular the detection oligonucleotides, are labeled with a first fluorescent dye and/or the solid support is labeled with a second fluorescent dye. Typical dyes include rhodamine dyes such as rhodamine-6-G, tetramethylrhodamine or rhodamine green, oxazine dyes, fluorescein, and the like.

When detecting nucleic acid analytes, it is preferred that in a first step a hybrid between detection oligonucleotides and analytes is formed. This complex is bound to the solid support via the hybridization of the analyte to capture oligonucleotides. The concentration of the detection oligonucleotides should not be the limiting factor in this first hybridization reaction. Therefore, the detection oligonucleotides are typically added to the sample in high amounts because the actual amount of analyte is usually unknown. After the hybridization reaction between detection oligonucleotides and analytes is completed, usually surplus detection oligonucleotides not being bound to the analyte are present. The emission of the first reporter of these unbound detection oligonucleotides is the main cause of background signal, deteriorating the reliability of analysis. According to the present invention, the detection of detection oligonucleotides is conducted in the presence of quenching oligonucleotides hybridizing to surplus detection oligonucleotides not being bound to the analyte and thereby quenching at least partially an emission of the first reporter of said surplus detection oligonucleotides. It is preferred that the hybrid between detection oligonucleotides and analyte has a higher melting temperature than a hybrid between detection oligonucleotides and quenching oligonucleotides. Therefore, the complete method can be conducted at two different temperatures so that competition of quenching oligonucleotides with analyte can be avoided. The melting temperature of the hybrid between detection oligonucleotides and analyte is at least 1° C., more preferably at least 2° C., even more preferably at least 5° C. and most preferably at least 10° C. higher than the melting temperature of the hybrid between detection oligonucleotides and quenching oligonucleotides under test conditions. Generally speaking, contacting the sample with the detection oligonucleotides is performed under first hybridization conditions allowing the generation of a stable hybrid between detection oligonucleotides and analyte. Contacting the sample with the quenching oligonucleotides is performed under second hybridization conditions allowing the generation of a stable hybrid between surplus detection oligonucleotides not being bound to the analyte and quenching oligonucleotides. Said second hybridization conditions do not destabilize the hybrid between detection oligonucleotides and analyte formed under said first hybridization conditions.

In a preferred embodiment, the capture probes, in particular the capture oligonucleotides, are covalently bound to the solid support. It is however alternatively also possible to utilize capture probes, in particular capture oligonucleotides, which are capable of binding to the solid support via affinity interaction. In this instance, the capture probes/capture oligonucleotides comprise a first affinity unit capable of binding to a second affinity unit attached to the solid support. As a typical example, the first affinity unit might be biotin and the second affinity unit might be streptavidin or avidin.

A typical solid support may be a bead, a cell, a pollen, or a plurality thereof. In a convenient embodiment of the invention, streptavidin coated polystyrene beads (from Spherotech, Libertyville, Ill. 60048) are used having a diameter of about 6 µm. According to the invention, the analyte is bound to the support by a capture probe. The capture probe of the invention may comprise a first portion bound to the support and a second portion capable of binding the analyte. Each support may comprise a multitude of capture probes.

However, it is also possible to utilize as a solid support the bottom of a sample carrier such as a slide or a titerplate. In this case, it is preferable to attach the capture probes covalently to discrete spots on such carrier or to attach the above mentioned second affinity unit thereto.

Typically, the first reporter labeling the detection probes/detection oligonucleotides differs from the second reporter labeling the solid support in its excitation wavelength and/or its emission wavelength. When choosing the reporters in such a way as to have different emission wavelengths (e.g. dyes emitting light at a wavelength of 565 nm for the first reporter and 690 nm for the second reporter; see examples below), these can be easily distinguished during detection. However, it is also possible to utilize reporters with different excitation wavelengths but the same emission wavelength. In this case, the first reporter and the second reporter are excited at different points in time and their emission is recorded correspondingly. Due to the time difference, the detected signal can be correlated to the different reporters. The difference in the excitation wavelength and/or emission wavelength between first and second reporter is typically at least 10 nm, preferably at least 20 nm, even more preferably at least 50 nm and most preferably at least 100 nm.

It is also preferred that the detection oligonucleotides comprise a linker sequence. This linker sequence links the sequence of the detection oligonucleotide complementary to the analyte with the first reporter. The capture oligonucleotides may also comprise a linker sequence, linking the sequence of the capture oligonucleotide complementary to analyte with the affinity unit or the solid support (see e.g. the T15 linker mentioned in the examples below). The use of the linker sequences serves to spatially separate the first and second reporter from each other (in the complex of detection oligonucleotides/analyte/capture oligonucleotides/solid support labeled with second reporter). Otherwise unfavorable interactions between these reporters may occur (e.g. FRET) which may reduce the signal emitted by the first reporter used to detect and quantify the analyte.

In an additional embodiment, the present invention is utilized in a multiplex format. At least two different analytes may be detected by providing at least two different sets of detection probes/detection oligonucleotides and at least two different sets of capture probes/capture oligonucleotides. The first set of detection oligonucleotides is complementary to the first analyte and the second set of detection oligonucleotides is complementary to the second analyte. The same applies to the capture oligonucleotides, accordingly. The different sets of detection probes/detection oligonucleotides are preferably labeled with different reporters. The reporters of one set are identical, have the same excitation wavelength and/or the same emission wavelength. Alternatively, the reporters of the detection probes/detection oligonucleotides are identical in the different sets. In this instance, it is preferred to utilize two different types of solid supports. The first analyte may be captured on the first solid support (such as a small bead) by a first affinity interaction. The second analyte may be captured on the second solid support (such as a large bead) by a second affinity interaction. The solid supports may be differentiated from each other by applying image analysis tools. Detecting the detection oligonucleotides bound to the first analyte can be conducted by utilizing a mask of the small beads whereas detecting the detection oligonucleotides bound to the second analyte can be conducted by utilizing a mask of the large beads.

According to the present invention, the detection of the detection probes/detection oligonucleotides can be performed applying imaging in combination with the generation of a mask. The solid support is labeled with a second reporter different from the one utilized to label the detection probes/detection oligonucleotides. An image is recorded at the emission wavelength of said second reporter. Thereafter, a mask is generated and applied to an image of the sample used for the above mentioned detection. It is preferred that the image recorded at the emission wavelength of the second reporter is recorded simultaneously with the image used for detecting the detection probes/detection oligonucleotides utilizing two detectors. This latter image is typically recorded at a wavelength different from the emission wavelength of the second reporter (see FIG. 5 below). The image of the sample used for detecting the detection probes/detection oligonucleotides typically is acquired at the emission wavelength of the first reporter. It is preferred to correct the image recorded at the emission wavelength of the second reporter in such a way that it spatially matches with the image used for detecting the detection probes/detection oligonucleotides. Alternatively, the latter image may be corrected to match the first image.

In another preferred embodiment, the quenching probes/quenching oligonucleotides comprise a quenching unit, said quenching unit preferably being a dye. In particular, the first reporter is a donor of a Förster resonance energy transfer (FRET) donor-acceptor-pair and the quenching unit is an acceptor of said donor-acceptor-pair. Alternatively, the quenching unit is a dark quencher which quenches at least partially the emission of the first reporter by dissipating the energy of the excited state of the first reporter into the environment.

When quantifying the analyte, such quantification may be performed by determining an amount of detection probes/detection oligonucleotides bound to the analyte. The signal stemming from the first reporter labeling such bound probes (in the complex of detection probe/analyte/capture probe/solid support) is related to the amount of the analyte. The amount of detection probes/detection oligonucleotides bound to the analyte may be expressed as the emission intensity emitted by the first reporter.

The method according to the present invention preferably comprises the additional step of determining an intensity of a background emission in the vicinity of the solid support and considering such intensity when determining the amount of detection probes/detection oligonucleotides.

In general, the detection probes may be aptameres, oligonucleotides, or antibodies. Analytes may be proteins or nucleic acids, in particular mRNA. The sample potentially comprising the analyte may be a cell lysate, in particular a crude cell lysate, or an in vitro prepared sample. The method according to the present invention is particularly useful in screening for potentially pharmaceutically active substances, in diagnostics, or in determining any potential side effects of drugs.

As already outlined above, in the case that the probe having the first reporter is a fluorescent probe and there are only a few analytes present it normally happens that the probe is present in an excess. Non-bound probe then emits fluorescent light which may cause a lowering of the sensitivity of the measurement. Imaging can preferably be performed utilizing confocal optics. Confocal optics spatially limit the measurement volume to a very narrow well-defined focal plane thus reducing background signals. In addition, it is advantageous to add a quencher of a fluorescence of the first reporter unit and to reduce the background thereby. Due to utilizing quenching oligonucleotides complementary to the detection oligonucleotides and applying the above described specific hybridization conditions, it is possible to specifically quench the background fluorescence of the unbound detection oligonucleotides. This is done without quenching the signal fluorescence of the detection oligonucleotides bound to the analyte.

Additionally, the background signal can be eliminated by mathematical methods. For example, the background signal is quantified in the vicinity of the solid support (though having sufficient distance to it) and subtracted from the signal of first reporter.

The probe having the first reporter is used for detecting the actual analyte, whereas the second reporter serves as marker for the solid support itself to which the analyte is bound, if present. Thus, the second reporter allows the localization of the solid support and the subsequent generation of a mask which improves the accuracy of the measurement. In a preferred embodiment, the reporter are dyes having different absorption maxima and/or, if they are fluorescent dyes, different emission spectra. The skilled person readily understands how to choose the dyes according to the fluorescent filters in the measuring device which filters separate the excitation and/or emission bands of the two dyes.

In the following a brief description of the figures is given.

Figure 7:
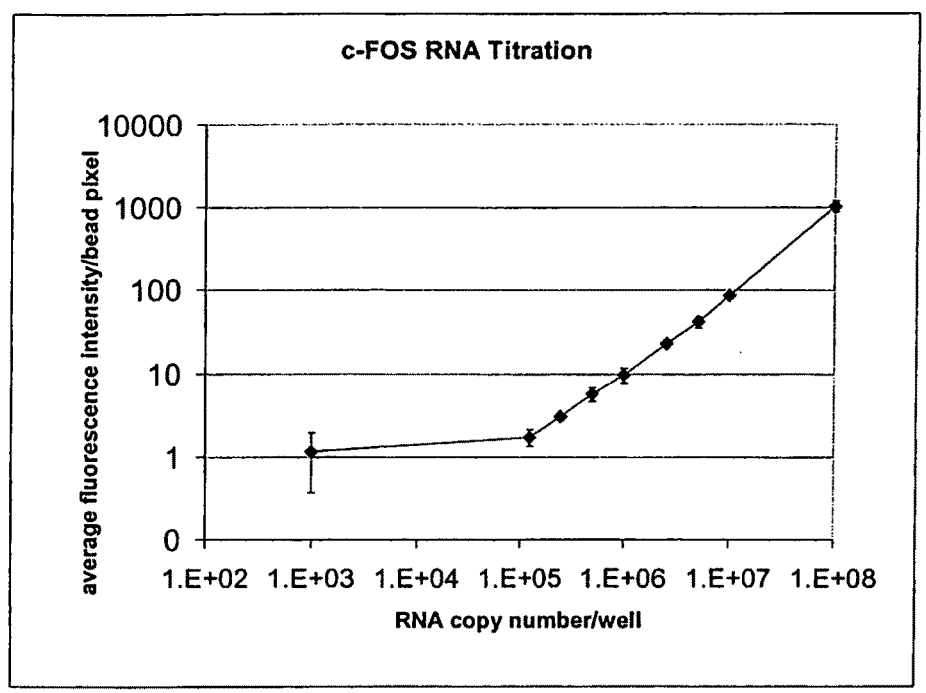

FIG. 7 depicts the results of c-fos RNA titration. Due to the logarithmic scale, the control is represented as $1*10^3$ copies (though in fact it does not contain any in vitro prepared c-fos RNA). The average fluorescence intensity per bead pixel relates to the amount of c-fos RNA analyte labeled with detection oligonucleotides and bound to the beads via the capture oligonucleotides.

Figure 8:
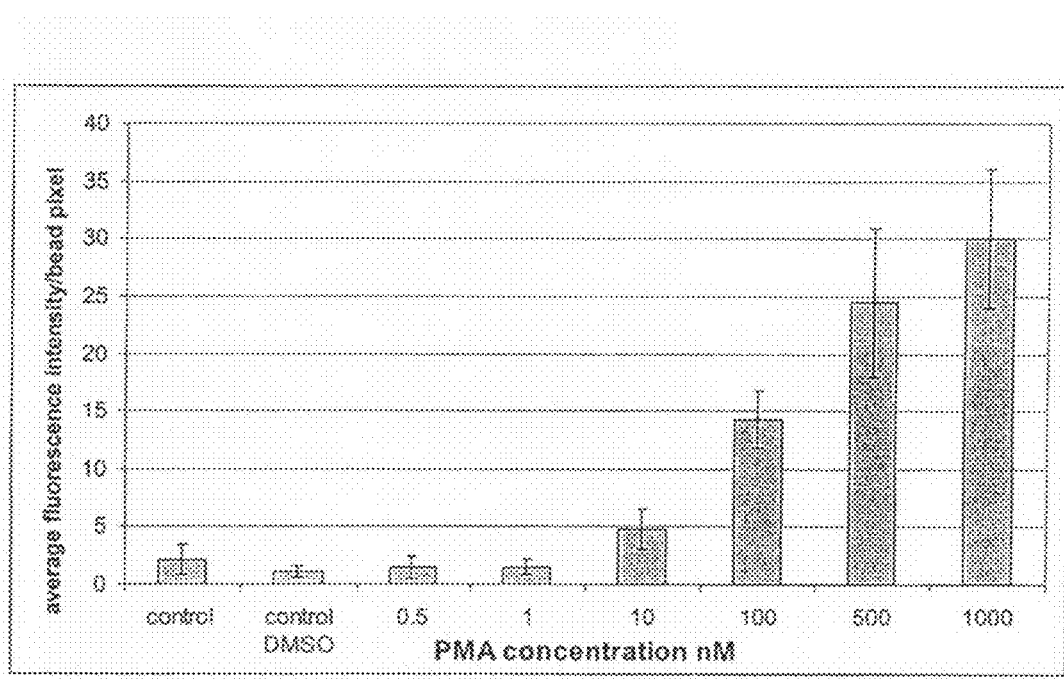

FIG. 8 shows the average fluorescence intensity per bead pixel at various PMA concentrations (c-fos experiments). The fluorescence intensity depicted in this FIG. 8 stems from emission of the detection oligonucleotides bound indirectly to the bead (via the analyte/capture oligonucleotide; see also FIGS. 1 and 2).

Figure 9:
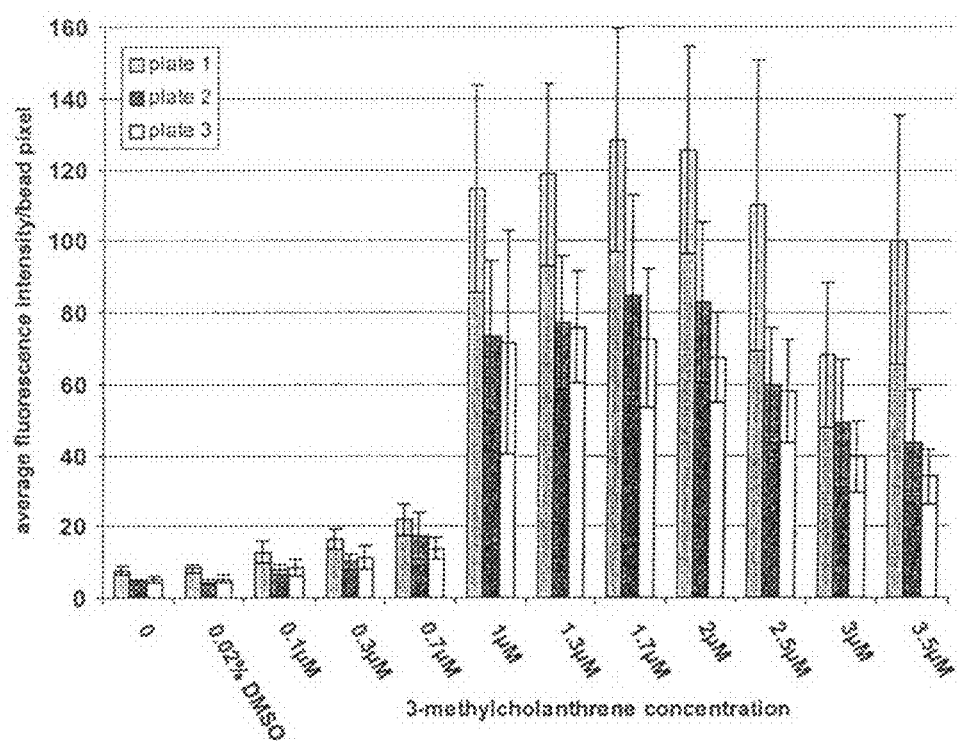

FIG. 9 shows the average fluorescence intensity per bead pixel at various 3-methylcholanthrene concentrations (cyp1A1 experiments). The fluorescence intensity depicted in this FIG. 9 stems from emission of the detection oligonucleotides bound indirectly to the bead (via the analyte/capture oligonucleotide; see also FIGS. 1 and 2). The results of measuring three sample plates are depicted (see also example 2).

Figure 10:
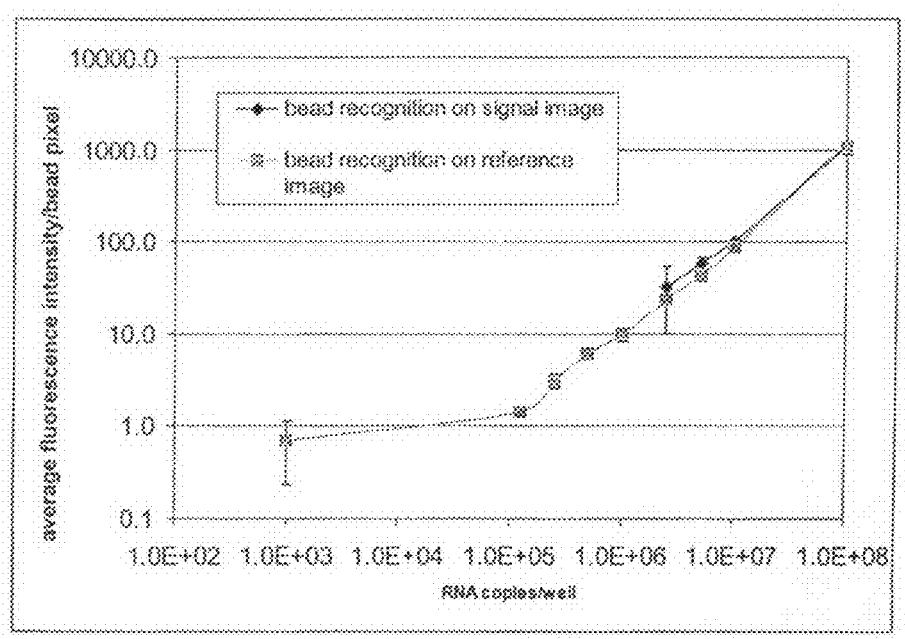

FIG. 10 relates to example 1a. It shows the average fluorescence intensity of the emission of the reporter labeling the detection oligonucleotides per bead pixel as a function of RNA copies per well (average of 4 wells per concentration). Due to the logarithmic scale, the control is represented as 1E+03 RNA copies/well. Two different kinds of image analysis have been performed. In the first analysis, the bead recognition was performed on the signal image obtained at the emission wavelength of the dye labeling the detection oligonucleotides. In the second analysis, the bead recognition was performed on the respective reference image obtained at the emission wavelength of the dye labeling the beads. The signal emission is related to the mRNA analyte concentration and thus decreases with decreasing mRNA concentration. This results in deteriorated bead recognition starting at a concentration of $5*10^6$ copies/RNA (note the high standard deviation) and no bead recognition at all at concentrations below. This significantly deteriorates the lower detection limit and sensitivity of the assay. The corresponding images underlying this figure are shown in FIG. 11.

Figure 11:
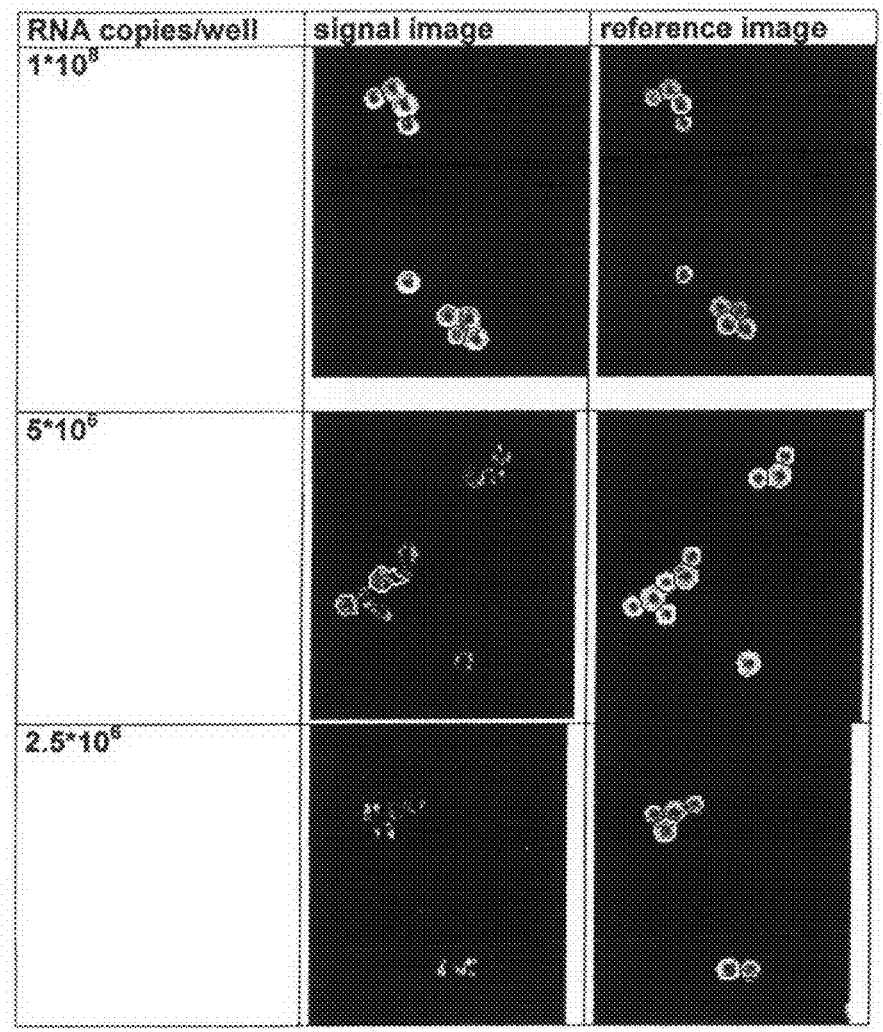

FIG. 11 relates to example 1a. Representative images from the image analysis of experiments depicted in FIGS. 7 and 10 are shown. FIG. 11 shows the results of bead recognition performed on (i) signal images obtained at the emission wavelength of the dye labeling the detection oligonucleotides and (ii) reference images obtained at the emission wavelength of the dye labeling the beads, at different concentrations of the target c-fos RNA analyte. The left column demonstrates that a reliable bead recognition performed on signal images is possible only in case of high analyte concentrations. At lower concentrations in the order of $2.5*10^6$ RNA copies/well, beads are not recognizable anymore. This kind of bead recognition corresponds to an experimental set-up conducted without the use of the second dye for labeling the beads (independently of the analyte concentration). The right column demonstrates that the bead recognition performed on reference images functions independently of analyte concentration.

Figure 12:
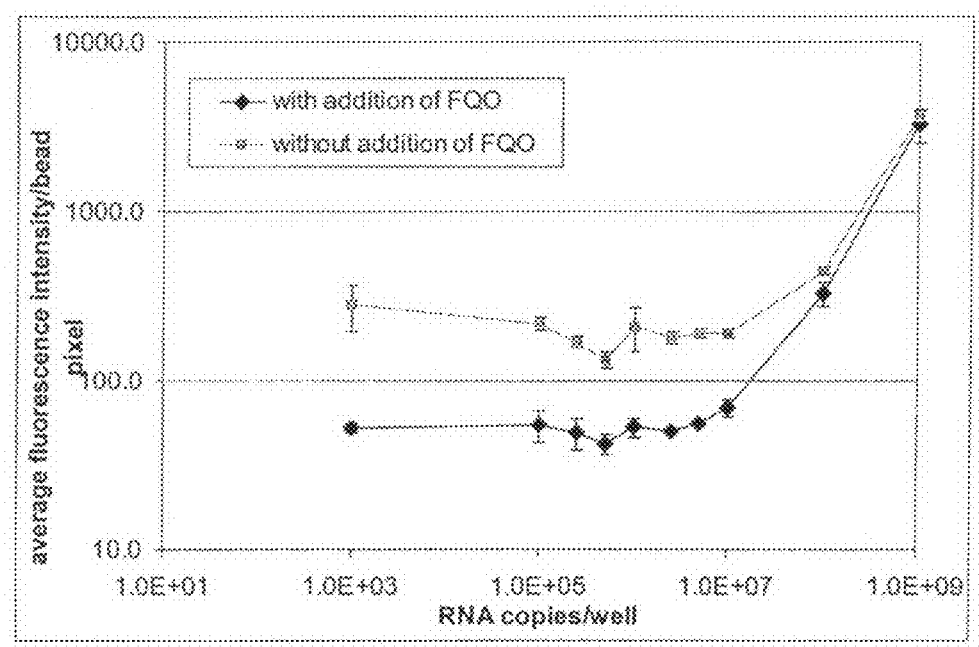

FIG. 12 shows the results of c-fos RNA titration with and without FQO (see also example 4). Due to the logarithmic scale, the control is represented as $1*10^3$ copies (though in fact it does not contain any in vitro prepared c-fos RNA). The average fluorescence intensity at the emission wavelength of the first reporter per bead pixel relates to the amount of c-fos RNA analyte labeled with detection oligonucleotides and bound to the beads via the capture oligonucleotides. The figure demonstrates that the dynamic range of the signal fluorescence intensity is significantly broader in the presence of FQO than in its absence. Consequently, the lower detection limit for the analyte is improved in the presence of FQO.

The figures and various experiments conducted according to the present invention are explained in more detail in the following.

Figure 1:
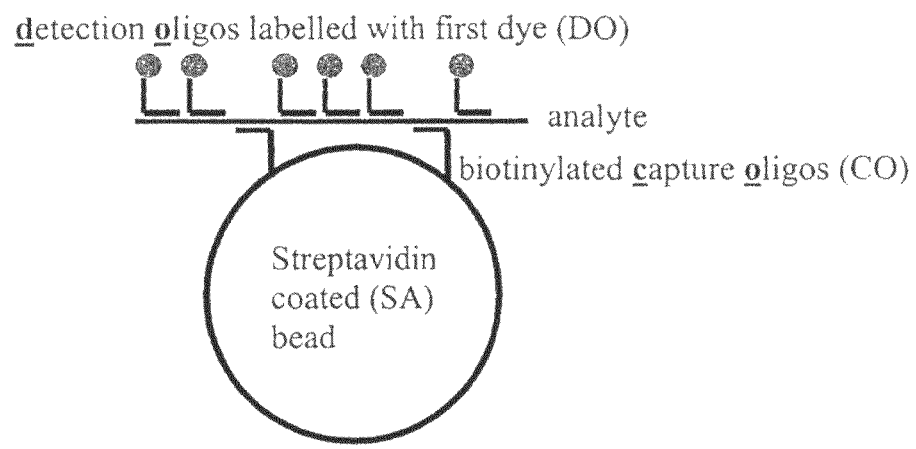
FIG. 1 depicts the result of a hybridization reaction utilizing detection oligonucleotides (DO), capture oligonucleotides (CO) and beads to detect a nucleic acid.

FIG. 1 depicts schematically that detection oligonucleotides (DO) labeled with a first dye are used to label the analyte nucleic acid. The resulting labeled complex is captured to streptavidin coated beads via hybridization of biotinylated capture oligonucleotides (CO). The use of a bead or other solid support is advantageous because the analyte is concentrated thereon.

Figure 2:
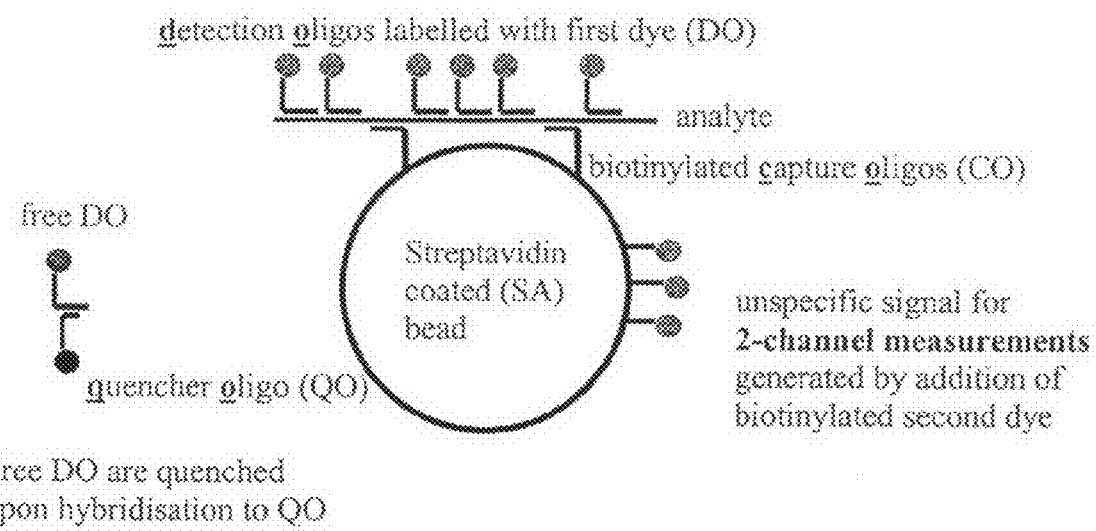
FIG. 2 depicts the measures taught by the present invention to improve the sensitivity of the assay principle shown in FIG. 1.

FIG. 2 depicts measures according to the present invention that are taken alone or in combination to reach an improved sensitivity of the assay. The streptavidin coated beads may be labeled by biotinylated second dyes to allow their reliable detection independent of the analyte concentration. So called 2-channel measurements can be conducted by detecting both the signal of the labeled detection oligonucleotides bound to the analyte-CO-bead complex and the reference emission of the biotinylated second dye. In addition or alternatively, the background signal caused by unbound fluorescent detection oligonucleotides may be minimized using quencher oligonucleotides hybridizing to the free surplus detection oligonucleotides.

Figure 3:
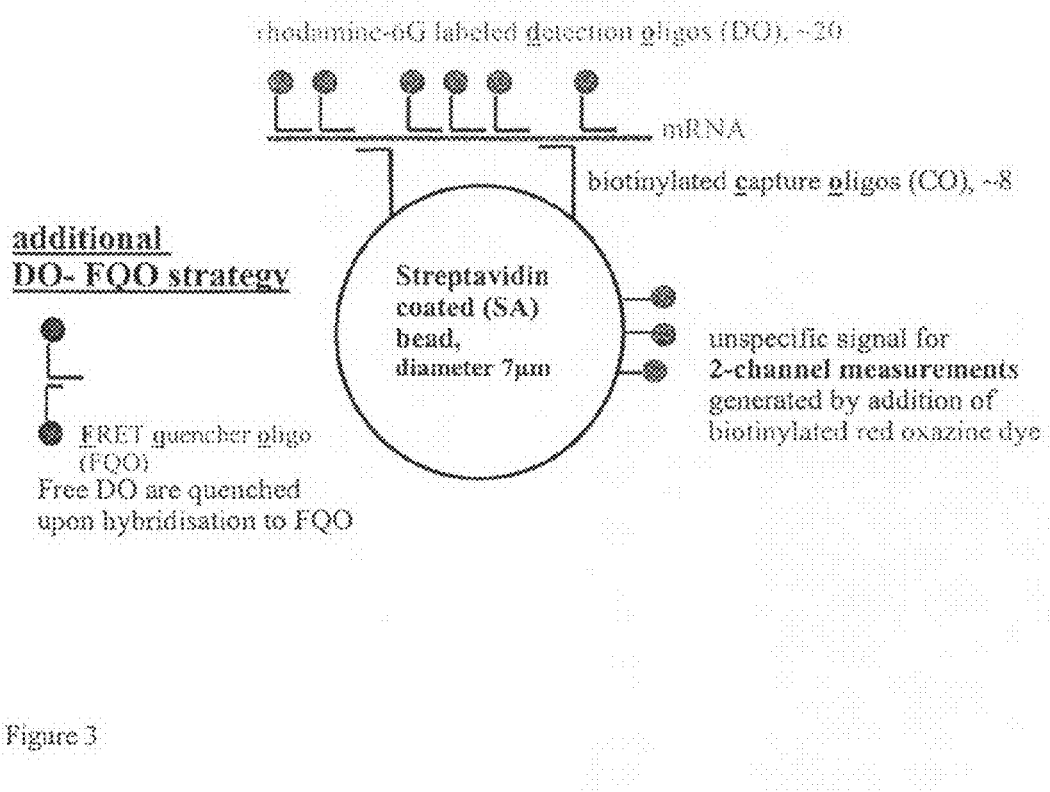
FIG. 3 shows an embodiment of the improved assay principle applying detection oligonucleotides labeled with rhodamine-6G, FRET quencher oligonucleotides and beads labeled with a red oxazine dye.

A specific embodiment of the assay principle according to the present invention is depicted in more detail in FIG. 3. A number of about 20 detection oligonucleotides (DO) marked with the fluorescent dye rhodamine-6G is used to label the target mRNA, i.e. the analyte, specifically. The resulting fluorescent complex is captured to streptavidin coated beads via hybridization of biotinylated so-called capture oligonucleotides (CO). The fluorescence intensity on the beads may be recorded using high speed dual channel confocal imaging. The fluorescence intensity of the detection oligonucleotides bound indirectly to the beads (via analyte/CO-complex) is linearly related to the mRNA concentration. To reach an improved sensitivity of the assay, additional steps can be taken according to the present invention, namely the unspecific labeling of the beads with a second color (such as biotinylated red oxazine dye) to allow their reliable detection independently of the RNA concentration. Furthermore, the background fluorescence caused by free surplus detection oligonucleotides can be minimized using FRET quencher oligonucleotides (FQO).

Figure 4:
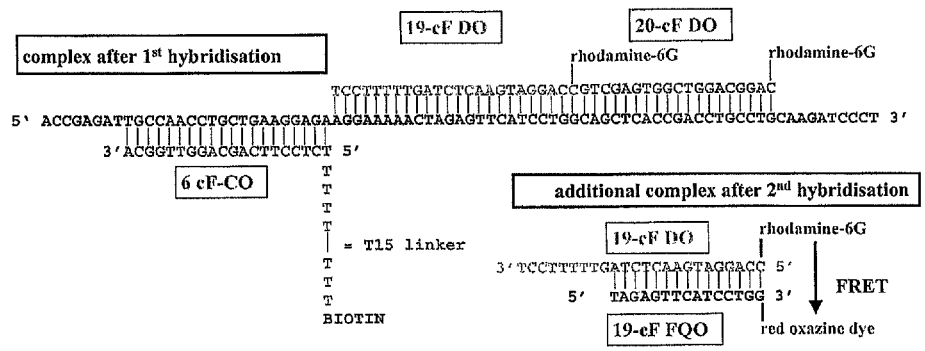
FIG. 4 depicts details of the assay principle taught by the present invention for the detection of c-fos mRNA (SEQ ID NO: 107), including sequences 19 cF-DO (SEQ ID NO: 19), 20 cF-DO (SEQ ID NO: 20), 6 cf-CO (SEQ ID NO: 6), and 19 cF-FQO (SEQ ID NO: 44).

An even more detailed example is given in FIG. 4: The c-fos mRNA is labeled with two detection oligonucleotides (19 cF-DO (SEQ ID NO: 19) and 20 cF-DO (SEQ ID NO: 20); for numbering of c-Fos oligonucleotides see Table 1). A biotinylated capture oligonucleotide (6 cf-CO) (SEQ ID NO: 6) serves for binding to the bead (bead not depicted). In addition (lower right corner), the quenching of surplus DO (19 cF-DO) (SEQ ID NO: 19) by its specific FQO (19 cF-FQO) (SEQ ID NO: 44) is demonstrated.

In the following, the present invention is explained in more detail by the following examples. The general procedures described in the following section "Material and methods" are applicable to all examples.

Material and Methods

Cell Culture

HepG2 hepatoma cells were maintained in DMEM-F12 (Gibco, catalogue no. 31331-028), supplemented with 10% FCS (Gibco, catalogue no. 10500-064) at 37° C. and 5% $CO_2$. A549 cells were maintained in DMEM-F12 (Gibco, catalogue no. 31331-028), supplemented with 5% FCS (Gibco, catalogue no. 10500-064) at 37° C. and 5% $CO_2$.

Preparation of Lysis Buffer

The lysis buffer contained DEPC-treated water (RNase free) with 100 mM Tris/HCl pH 8.0, 10 mM EDTA pH 8.0, 0.5 M LiCl, 5 mM DTT, 1% (w/v) LiDS and 1 mg/ml Proteinase K (Roche Diagnostics, catalogue no. 1000144). A stock solution of the lysis buffer without Proteinase K was prepared and stored at −20° C., freshly prepared Proteinase K was added before each experiment. All chemicals were purchased in highest quality ("for molecular biology") from Sigma-Aldrich.

Streptavidin Coated Beads

Streptavidin coated polystyrene beads (SA beads) with a diameter of 6.7 μm and a concentration of $3.8*10^4$ beads/pi were purchased from Spherotech (Cat. No. SVP-60-5).

Preparation of Biotinylated Red Oxazine Dye

A red oxazine dye was biotinylated using standard procedures. A 50 μM stock solution of the biotinylated red oxazine dye in DMSO was prepared.

Detection

Fully automated dual-channel confocal imaging was performed with two independent cooled CCD detectors. Excitation wavelengths were 532 nm and 633 nm, a dichroic beam splitter with 630 nm was used and emission filters were 565/50 nm and 690/40 nm. Laser power was ~500 μW for both wavelengths, measured at the entrance of the objective. Exposure times were usually in the range of 500-1000 ms. 1-5 image pairs/well of a standard titerplate housing the sample were recorded, each image had a size of 445×336 μm.

In addition, correction images with appropriate dye solutions, pre-stained beads and dark images (detector noise)

were recorded. In combination with appropriate algorithms these images were used for correction of assay images with regard to camera noise and irregularities of illumination. Furthermore, the image pairs from detectors 1 and 2 were spatially adjusted to achieve optimal overlap.

Evaluation

An image of the sample was acquired at 565 nm by the first CCD detector. This image is called the signal image. At this wavelength, the emission of the detection oligonucleotides is seen. Therefore, in principle one can see the fluorescence emission of both the unbound detection oligonucleotides as well as the detection oligonucleotides bound specifically to the analyte (and consequently via the capture oligonucleotides to the beads). To distinguish these signals from each other, the present invention teaches to minimize the emission of the unbound detection oligonucleotides by the use of complementary quencher oligonucleotides. The signal intensity on the beads is linear dependent on the analyte concentration, i.e. in the present example the mRNA concentration.

Figure 5:
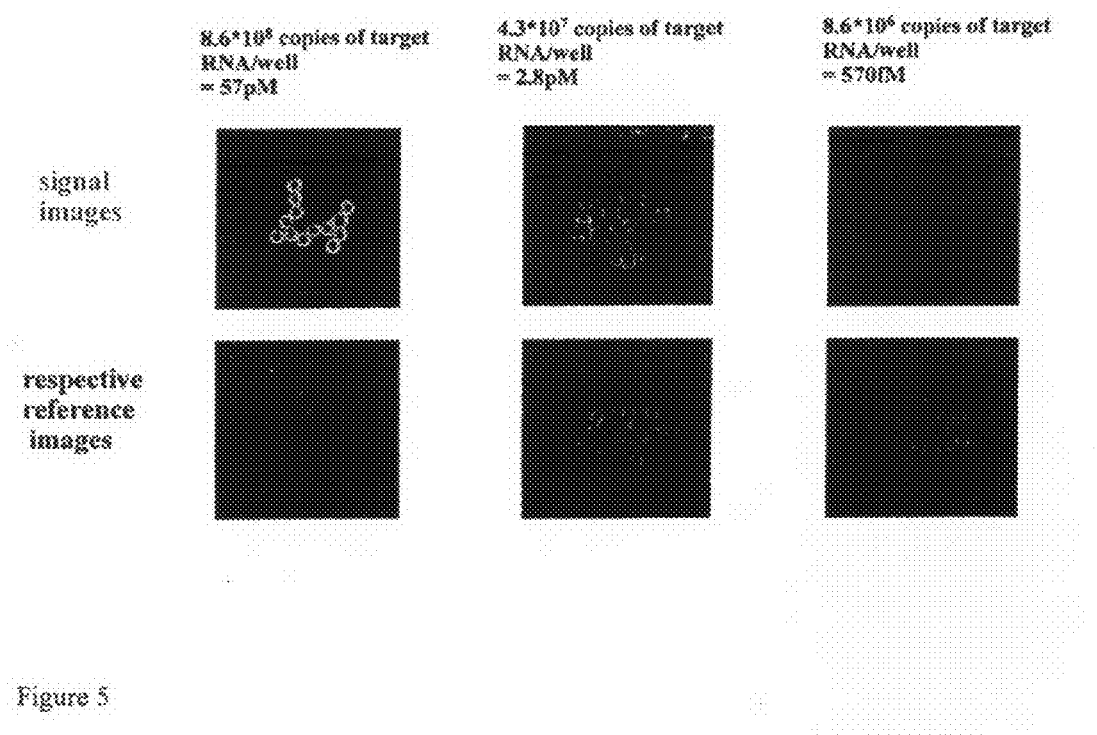
FIG. 5 shows signal images and reference images of beads at different concentrations of the target RNA analyte. The signal image was recorded at the emission wavelength of the first reporter labeling the detection oligonucleotides (565 nm), whereas the reference image was recorded at the emission wavelength of the second reporter labeling the beads (690 nm).

In addition, an image of the sample was acquired at 690 nm by the second CCD detector. This image is called the reference image. At this wavelength, the emission of the biotinylated red oxazine dye is seen. The fluorescence of the biotinylated red oxazine dye bound to the beads can be seen as a red ring in the reference image (see FIG. 6, left picture). This emission of the dyes bound to the beads can be distinguished from the background emission of the unbound biotinylated red oxazine dye through threshold techniques. This fluorescence intensity is constant and not dependent on the mRNA analyte concentration, see FIG. 5 for illustration. At extremely high mRNA concentrations it may become inversely related to the mRNA concentrations due to limited streptavidin binding sites, however, under physiological conditions and in the experiments presented here this was not the case.

Figure 6:
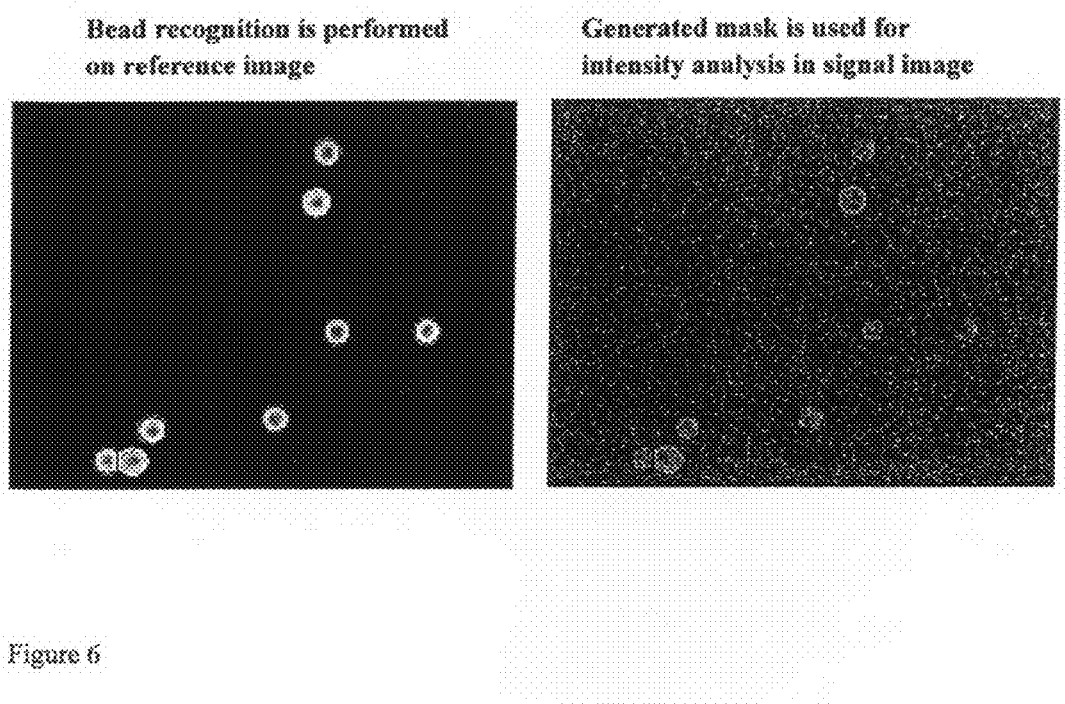
FIG. 6 shows a strategy for image analysis according to the present invention.

The analysis of the images was performed with image analysis software as follows. Segmentation of the beads from the background was performed on a pixel-basis in the reference image. As can be seen in FIG. 6 (left picture), detected beads are marked by a ring. A mask of these rings corresponding to detected beads was generated from the reference image. This mask was applied to the signal image (see FIG. 6, right picture). Areas within the outer boundary of the ring were evaluated for fluorescence intensity stemming from the DO-analyte-CO complex bound to the bead. It was particularly advantageous to further reduce distorting background signals of free DO not completely quenched by determining the local background intensity in a circular region near every single bead in the signal image. Such local background intensity was then subtracted from the signal intensity.

The final result was the mean fluorescence intensity/bead pixel of the signal image. In general, the intensity was averaged over all correctly detected beads of the image. The beads were usually comprised in wells of micro- or nanotiter plates and in some cases, several images were taken of each well. In this instance, the intensity was averaged over all images of one well.

EXAMPLE 1

Detection of c-fos mRNA

Preparation of Oligonucleotides (DO, CO, UO and FQO)

A set of 19 detection oligonucleotides (DO) and 8 capture oligonucleotides (CO) was chosen. The DO were labeled with rhodamine-6G at the 5' terminus. The CO comprised a nucleotide sequence complementary to a sequence of the analyte, a T15-linker at the 5' terminus and biotin. The oligonucleotides were complementary to parts of the nucleotide sequence of the c-fos mRNA, had a minimal melting temperature Tm of 63° C. with a length varying between 17-26 nucleotides (nt), depending on GC-content. They covered a 676 nt long part of the c-fos mRNA (total length 1143 nt) between nucleotides 161 and 837 without intervening gaps. The DO and CO were chosen in such a way that they were not complementary to each other (DO and CO being complementary to each other would result in unspecific binding of DO to the beads via their direct binding to CO). 6 additional oligonucleotides had a too high degree of complementarity to others and were not labeled. These unlabeled oligonucleotides (UO) were nevertheless prepared and added to the hybridization solution to ensure that the respective part of the c-fos mRNA was completely covered and thus in a double-stranded, more stable conformation. The CO were chosen in a way that they were spaced relatively evenly between the DO. Furthermore, every DO was chosen to have the nucleotide A, C or T at the 5' terminus, because G is a known quencher of rhodamine-6G fluorescence.

In addition, a set of 19 FRET (Förster resonance energy transfer) quencher oligonucleotides (FQO) was prepared. These were complementary to the 5' terminal part of the respective DO, however, they were only 15 nt long, resulting in a lower minimal melting temperature Tm of ~42° C. They were labeled with a red oxazine dye at the 3' terminus. All oligonucleotides were synthesized according to standard procedures.

Stock solutions of oligonucleotides were prepared in TE-buffer (DEPC-treated water with 10 mM Tris-HCl, 1 mM EDTA pH 8.0) at a concentration of 100 µM and frozen at −80° C. DO-, CO-, UO- and FQO-mixtures were prepared (by adding equal amounts of each oligonucleotide solution) at a concentration of 100 µM. The DO-mixture comprised 19 different detection oligonucleotides, each individual oligonucleotide in this mixture was present at a concentration of 5.26 µM. For the FQO-mixture, the concentration of each individual oligonucleotide (FQO) was also 5.26 µM, whereas the individual concentration of each CO was 12.5 µM for CO-mixture and the individual concentration of each UO was 16.66 µM for UO-mixture.

The following table 1 shows a complete list of all oligonucleotides used for the detection of c-fos mRNA analyte. The position given below for the CO, DO and UO refers to the position on a DNA strand complementary to the mRNA analyte.

TABLE 1

List of oligonucleotides used for the detection of c-fos mRNA

| position | name | sequence |
|---|---|---|
| 8 CO (capture oligonucleotides) comprising a linker of 15 T-nucleotides (T15) and biotin attached to 5' terminus ||| 
| 258-276 | 1 cF-CO | Biotin-5'-T15-ggctctggtctgcgatggg-3' |
| 277-296 | 2 cF-CO | Biotin-5'-T15-gggactccgaaagggtgagg-3' |

TABLE 1-continued

List of oligonucleotides used for the detection of c-fos mRNA

| position | name | sequence |
|---|---|---|
| 394-420 | 3 cF-CO | Biotin-5'-T15-ccttttctcttcttcttctggagataa-3' |
| 421-441 | 4 cF-CO | Biotin-5'-T15-attcctttcccttcggattct-3' |
| 528-548 | 5 cF-CO | Biotin-5'-T15-atctcggtctgcaaagcagac-3' |
| 549-568 | 6 cF-CO | Biotin-5'-T15-tctccttcagcaggttggca-3' |
| 633-655 | 7 cF-CO | Biotin-5'-T15-ccacagacatctcttctgggaag-3' |
| 656-676 | 8 cF-CO | Biotin-5'-T15-ccccagtcagatcaagggaag-3' |

19 DO (detection oligos 5' labeled with rhodamine-6G (Rh6G)

| position | name | sequence |
|---|---|---|
| 161-182 | 9 cF-DO | Rh6G-5'-atgaagttggcactggagacgg-3' |
| 183-200 | 10 cF-DO | Rh6G-5'-atggcagtgaccgtggga-3' |
| 201-219 | 11 cF-DO | Rh6G-5'-caggtccggactggtcgag-3' |
| 220-238 | 12 cF-DO | Rh6G-5'-cgggctgcaccagccactg-3' |
| 312-329 | 13 cF-DO | Rh6G-5'-ccagccctggagtaagcc-3' |
| 330-352 | 14 cF-DO | Rh6G-5'-ctcctgtcatggtcttcacaacg-3' |
| 353-371 | 15 cF-DO | Rh6G-5'-ccaatgctctgcgctcggc-3' |
| 372-393 | 16 cF-DO | Rh6G-5'-ctgttccaccttgcccctcctg-3' |
| 462-478 | 17 cF-DO | Rh6G-5'-ccctcctccggttgcgg-3' |
| 479-501 | 18 cF-DO | Rh6G-5'-cgcttggagtgtatcagtcagct-3' |
| 569-592 | 19 cF-DO | Rh6G-5'-ccaggatgaactctagttttcct-3' |
| 593-611 | 20 cF-DO | Rh6G-5'-caggcaggtcggtgagctg-3' |
| 612-632 | 21 cF-DO | Rh6G-5'-cccaggtcatcagggatcttg-3' |
| 696-715 | 22 cF-DO | Rh6G-5'-aggcctcctcagactccggg-3' |
| 716-733 | 23 cF-DO | Rh6G-5'-tgaggagaggcagggtga-3' |
| 734-754 | 24 cF-DO | Rh6G-5'-agggcttgggctcagggtcat-3' |
| 755-775 | 25 cF-DO | Rh6G-5'-tgctcttgacaggttccactg-3' |
| 796-815 | 26 cF-DO | Rh6G-5'-aagtcatcaaagggctcggt-3' |
| 816-837 | 27 cF-DO | Rh6G-5'-cctggatgatgctgggaacagg-3' |

6 UO (unlabeled oligonucleotides)

| position | name | sequence |
|---|---|---|
| 239-257 | 28 cF-UO | 5'-gccacagaggagacgaggg-3' |
| 297-311 | 29 cF-UO | 5'-ccagcggaggggggcg-3' |
| 442-461 | 30 cF-UO | 5'-catttggctgcagccatctt-3' |
| 502-527 | 31 cF-UO | 5'-ttctcatcttctagttggtctgtctc-3' |
| 677-695 | 32 cF-UO | 5'-gtggcaacctctggcaggc-3' |
| 776-795 | 33 cF-UO | 5'-cttcagctccatgctgctga-3' |

19 FQO (FRET quencher oligos) 3' labeled with red oxazine dye (RO)

| position | name | sequence |
|---|---|---|
| 9 cF-DO | 9 cF-FQO | 5'-cag tgc caa ctt cat-3'-RO |
| 10 cF-DO | 10 cF-FQO | 5'-cac ggt cac tgc cat-3'-RO |
| 11 cF-DO | 11 cF-FQO | 5'-acc agt ccg gac ctg-3'-RO |
| 12 cF-DO | 12 cF-FQO | 5'-ggc tgg tgc agc ccg-3'-RO |

TABLE 1-continued

List of oligonucleotides used for the detection of c-fos mRNA

| position | name | sequence |
|---|---|---|
| 13 cF-DO 13 | cF-FQO | 5'-tta ctc cag ggc tgg-3'-RO |
| 14 cF-DO 14 | cF-FQO | 5'-aga cca tga cag gag-3'-RO |
| 15 cF-DO 15 | cF-FQO | 5'-agc gca gag cat tgg-3'-RO |
| 16 cF-DO 16 | cF-FQO | 5'-ggc aag gtg gaa cag-3'-RO |
| 17 cF-DO 17 | cF-FQO | 5'-gca acc gga gga ggg-3'-RO |
| 18 cF-DO 18 | cF-FQO | 5'-gat aca ctc caa gcg-3'-RO |
| 19 cF-DO 19 | cF-FQO | 5'-tag agt tca tcc tgg-3'-RO |
| 20 cF-DO 20 | cF-FQO | 5'-tca ccg acc tgc ctg-3'-RO |
| 21 cF-DO 21 | cF-FQO | 5'-ccc tga tga cct ggg-3'-RO |
| 22 cF-DO 22 | cF-FQO | 5'-agt ctg agg agg cct-3'-RO |
| 23 cF-DO 23 | cF-FQO | 5'-ccc tgc ctc tcc tca-3'-RO |
| 24 cF-DO 24 | cF-FQO | 5'-ctg agc cca agc cct-3'-RO |
| 25 cF-DO 25 | cF-FQO | 5'-aac ctg tca aga gca-3'-RO |
| 26 cF-DO 26 | cF-FQO | 5'-gcc ctt tga tga ctt-3'-RO |
| 27 cF-DO 27 | cF-FQO | 5'-cca gca tca tcc agg-3'-RO |

EXAMPLE 1a c-fos RNA Titration

In Vitro Preparation of c-Fos RNA

A549 cells were stimulated with a cytokine mixture (16.5 ng/ml IFN-γ, 41.7 ng/ml IL-1β and 25 ng/ml TNF-α) to induce c-fos mRNA expression. After 1 h the total RNA was isolated (QIAGEN, RNeasy Mini Protocol for RNA Cleanup). Then the 1143 nucleotides long coding sequence of c-fos (Genbank Accession-number K00650) was prepared by RT-PCR with two specific primers (forward primer: 5' GCG AAT TCC TCG GGC TTC AAC GCA GA 3', reverse primer: 5' ATG GAT CCC AGC GTG GGT GAG CTG A 3'). These primers contained an additional BamHI and EcoRI restriction site, respectively. The success of the PCR was verified via Agarose gelelectrophoresis and the PCR product was purified (QIAquick PCR Purification Kit). The PCR product was cloned into the vector pBluescript II KS(+/−) using the EcoRI and BamHI restriction sites. The resulting product was used for transformation of E. coli Top10 F' cells, several clones were picked and amplified. The constructs were verified by complete sequencing and amplified in E. coli—TOP 10 F' cells, purified (QIAquick PCR Purification Kit) and then linearized using BamHI. The linearized probe was used for in vitro transcription of RNA (Promega, Riboprobe System—T3/T7 Kit) using T3 RNA Polymerase. The resulting product was subjected to DNAse digestion and afterwards purified (QIAGEN, RNeasy Mini Protocol for RNA Cleanup). The RNA amount was determined (Agilent 2001 Bioanalyzer) to be 901 ng/µl=2.2 µM=$1.35*10^{12}$ copies RNA/µl (mean value of five independent measurements). The molecular weight of c-fos RNA is 401280 g/Mol.

Preparation of C-Fos Control Lysate $3*10^6$ HepG2 cells were seeded on a 10 cm tissue culture plate (Greiner bio-one, catalogue no. 664160) in 10 ml DMEM-F12 (Gibco, catalogue no. 31331-028) supplemented with 10% FCS (Gibco, catalogue no. 10500-064) and incubated at 37° C. and 5% $CO_2$. After 48 hours the medium was changed to DMEM (Sigma, catalogue no. D 5921) supplemented with 0.1% sterile filtered HSA (Sigma, catalogue no. A 1653). After incubation for 24 h the medium was changed to DMEM supplemented with 0.1% HSA and 0.02% DMSO. No PMA (Phorbol 12-myristate 13-acetate) was added so that no c-fos expression was induced. The cells were incubated for 1 h at 37° C. and 5% $CO_2$. Then the medium was removed and 5 ml lysis buffer was added, incubated for 15 min at 37° C. and 5% $CO_2$ and then mixed by repeated pipetting. This control lysate was stored at −20° C.

Assay Procedure

The in vitro prepared RNA was diluted with control lysate to yield the 8 different copy numbers/24 µl indicated in Table 2 below. A hybridization solution was prepared using the CO, DO and UO mixture solutions described above. Appropriate volumes were added to lysis buffer to yield a final concentration of 7 nM of each CO, DO and UO. Furthermore, the hybridization solution contained $3.7*10^3$ SA beads/ml.

TABLE 2 c-fos RNA copy number/well

| copy number/24 µl (= copy number/well) | final RNA concentration |
|---|---|
| $1 * 10^8$ | 6.9 pM |
| $1 * 10^7$ | 692 fM |
| $5 * 10^6$ | 346 fM |
| $2.5 * 10^6$ | 173 fM |
| $1 * 10^6$ | 69 fM |
| $5 * 10^5$ | 34.6 fM |
| $2.5 * 10^5$ | 17.3 fM |
| $1 * 10^5$ | 6.9 fM |

Four 24 μl aliquots of each RNA dilution were transferred to the wells of a glass bottom, heat resistant measurement plate (NanoCarrier™96/30, Evotec Technologies), respectively. 4 additional wells were filled with 24 μl of control lysate. To each well, 1 μl of hybridization solution was added resulting in a final concentration of 0.28 nM of each DO, CO and UO. The final SA bead number per well was 3700. The measurement plate was placed into a humid incubator (Kendro, HERACELL 150/70 CO2 INKUBATOR VA 230V) and incubated over night (for approximately 17 h) at 53° C. After this first hybridization, a DO-analyte-CO-bead-complex was formed (see also the schematic drawing of FIG. 1).

The next day a quencher solution was prepared using the FQO mixture solution and the stock solution of biotinylated red oxazine dye described above. Appropriate volumes were added to lysis buffer to yield a final concentration of 72.8 nM of each FQO and a final concentration of 1.3 μM of the biotinylated red oxazine dye. 1 μl of the quencher solution was added to each well of the measurement plate, resulting in a final concentration of 2.8 nM for each FQO and 50 nM of the biotinylated red oxazine dye. The measurement plate was again placed into a humid incubator and incubated for 1 h at 35° C. After this second hybridization, a situation was achieved as depicted in FIG. 3. The emission of the free (unbound) detection oligonucleotides was quenched upon hybridization to the FRET quencher oligonucleotides. The biotinylated red oxazine dye served to generate a reference emission for the reliable detection of the beads. Then the plate was measured as described above.

Results

The results are listed in Table 3 and depicted in FIG. 7. The RNA copy number is linearly related to the fluorescence signal intensity of the detection oligonucleotides bound via analyte/capture oligonucleotides to the beads over a range of three orders of magnitude, namely between $10^5$-$10^8$ copies of RNA/well. (In fact the upper limit of the linear range is $10^9$ copies RNA/well, data not shown in FIG. 7; see FIG. 12). However, the lower detection limit is more relevant for typical applications and is in the range of $5*10^5$ copies of c-fos RNA or even below that can be distinguished reliably from the control. A linear fit of the data shown in FIG. 7 resulted in the equation $y=1.06*10^6x-3.444$. This calibration was used in example 1b for the calculation of mRNA copy number/cell.

TABLE 3

Results of c-fos RNA titration

| RNA copies | average fluorescence signal intensity/bead pixel | | | | | |
|---|---|---|---|---|---|---|
| | well | | | | | |
| | well 1 | well 2 | well 3 | well 4 | mean | standard deviation |
| $1.0*10^8$ | 912.8 | 1271.2 | 1010.1 | 943.9 | 1034.5 | 162.9 |
| $1.0*10^7$ | 95.3 | 86.3 | 84.0 | 81.1 | 86.7 | 6.1 |
| $5.0*10^6$ | 36.2 | 47.0 | 35.5 | 47.1 | 41.5 | 6.5 |
| $2.5*10^6$ | 24.5 | 24.2 | 22.1 | 20.6 | 22.8 | 1.8 |
| $1.0*10^6$ | 8.6 | 10.2 | 7.5 | 11.8 | 9.5 | 1.9 |
| $5.0*10^5$ | 5.1 | 4.5 | 6.4 | 6.9 | 5.7 | 1.1 |
| $2.5*10^5$ | 3.4 | 3.1 | 2.7 | 3.0 | 3.1 | 0.3 |
| $1.25*10^5$ | 2.3 | 1.4 | 1.5 | 1.8 | 1.7 | 0.4 |
| control ("$1*10^3$") | 2.1 | 1.7 | 0.5 | 0.5 | 1.2 | 0.8 |

EXAMPLE 1b

Expression of c-fos mRNA in HepG2 Cells

HepG2 cells were seeded at a density of $2*10^6$ cells in 10 ml medium/plate (corresponding to $2*10^5$ cells/ml) in nine 10 cm tissue culture plates (Greiner bio-one, catalogue no. 664160) in DMEM-F12 (Gibco, catalogue no. 31331-028) supplemented with 10% FCS (Gibco, catalogue no. 10500-064). The cells were incubated for 48 h at 37° C. with 5% $CO_2$. Then medium was changed to DMEM (Sigma, catalogue no. D 5921) supplemented with 0.1% sterile filtered HSA (Sigma, catalogue no. A 1653) and incubation was continued for 24 h at 37° C. with 5% $CO_2$. Then the cells were incubated with PMA (Phorbol 12-myristate 13-acetate, Sigma, catalogue no. P1585) for 1 h at 37° C. and 5% $CO_2$ to induce expression of c-fos. 500 μl of appropriate PMA dilutions in DMEM with 0.1% HSA were added, for final concentrations refer to table 4 below.

TABLE 4

PMA concentrations

| plate number | PMA concentration |
|---|---|
| 1 | 0 nM (control) |
| 2 | 0 nM, 0.1% DMSO (DMSO-control) |
| 3 | 0.5 nM |
| 4 | 1 nM |
| 5 | 10 nM |
| 6 | 100 nM |
| 7 | 500 nM |
| 8 | 1 μM |

One control plate was used for cell counting, the final cell number was $1.5*10^7$ cells/plate. After 1 h the stimulation mixture was removed and the cells were lysed by addition of 5 ml lysis buffer/plate, resulting in a cell number of $3*10^6$ cells/ml. Immediately after the addition of the lysis buffer the plates were put on ice and after 15 min stored at −20° C. for 24 h.

Assay Procedure

Eight 24 μl aliquots (each corresponding to $7.2*10^4$ lysed cells) of the cell lysate of each PMA concentration were added to the wells of a heat-resistant glass bottom plate (Nanocarrier™ 384/30, Evotec Technologies), respectively. A hybridization solution was prepared using the CO, DO and UO mixture solutions described above. Appropriate volumes were added to lysis buffer to yield a final concentration of 7 nM of each CO, DO and UO. Furthermore, the hybridization solution contained $3.7*10^3$ SA beads/ml.

To each well, 1 μl of hybridization solution was added resulting in a final concentration of 0.28 nM of each DO, CO and UO. The final SA bead number per well was 3700. The measurement plate was placed into a humid incubator (Kendro, HERACELL 150/70 CO2 INKUBATOR VA 230V) and incubated over night (for approximately 17 h) at 53° C.

The next day a quencher solution was prepared using the FQO mixture solution and the stock solution of biotinylated red oxazine dye described above. Appropriate volumes were added to lysis buffer to yield a final concentration of 72.8 nM of each FQO and a final concentration of 1.3 μM of the biotinylated red oxazine dye. 1 μl of the quencher solution was added to each well of the measurement plate, resulting in a final concentration of 2.8 nM for each FQO and 50 nM of the biotinylated red oxazine dye. The measurement plate was again placed into a humid incubator and incubated for 1 h at 35° C. Then the plate was measured as described above.

Results

The results are listed in Table 5 and depicted in FIG. 8.

With increasing PMA concentration (used to stimulate expression of c-fos mRNA) an increase in the average fluorescence intensity/bead pixel stemming from the detection oligonucleotide—mRNA analyte—capture oligonucleotide complex bound to beads can be observed. Thus, PMA induced a strong increase in c-fos expression with an $EC_{50}$ of 484 nM. This is in the same order of magnitude as the $EC_{50}$ that can be estimated from published results (Northern Blot) (Arts, J., Grimbergen, J., Bosma, P. J., Rahmsdorf, H. J., and Kooistra, T. (1996). Role of c-Jun and proximal phorbol 12-myristate-13-acetate-(PMA)-responsive elements in the regulation of basal and PMA-stimulated plasminogen-activator inhibitor-1 gene expression in HepG2. Eur. J. Biochem. 241, 393-402). The z' values (Zhang J H, Chung T D, Oldenburg K R: A Simple Statistical Parameter for Use in Evaluation and Validation of High Throughput Screening Assays. *J Biomol Screen* 1999; 4:67-73) are positive down to 100 nM PMA, thus the reliable differentiation between control and stimulated sample down to a concentration of 100 nM PMA in high throughput screening (HTS) is possible.

Using the calibration of example 1a, the measured fluorescence intensity at 100 nM PMA equals a copy number of $3.03*10^6$ copies mRNA/well (corresponding to 24 µl of lysate). Taking into account that 24 µl of lysate contained $7.2*10^4$ lysed cells (see above), an average expression rate of 42 copies mRNA/cell was concluded.

TABLE 5

Results of c-fos mRNA expression in HepG2 cells

| PMA concentration [nM] | Mean average fluorescence signal intensity/bead pixel | std | CV % | z' |
|---|---|---|---|---|
| 0 (control) | 2.15 | 1.31 | 60.68 | |
| 0 (control DMSO) | 1.09 | 0.51 | 47.17 | |
| 0.5 | 1.51 | 0.97 | 64.14 | −9.58 |
| 1 | 1.53 | 0.63 | 41.05 | −6.75 |
| 10 | 4.84 | 1.74 | 35.97 | −0.80 |
| 100 | 14.29 | 2.46 | 17.24 | 0.32 |
| 500 | 24.44 | 6.48 | 26.52 | 0.10 |
| 1000 | 30.03 | 5.97 | 19.89 | 0.33 |

EXAMPLE 2

Expression of cyp1A1 mRNA in HepG2 Cells

Preparation of Oligonucleotides (DO, Co and FQO)

A set of 20 detection oligonucleotides (DO) and 8 capture oligonucleotides (CO) was chosen. The DO were labeled with rhodamine-6G at the 5' terminus. The CO comprised a nucleotide sequence complementary to a sequence of the analyte, a T15-linker at the 5' terminus and biotin. The oligonucleotides were complementary to parts of the nucleotide sequence of the cyp1A1 mRNA, had a minimal melting temperature Tm of 63° C. (with the exception of two unlabelled oligonucleotides with a Tm of 55° C.) with a length varying between 18-25 nt (with the exception of an UO with less than 18 nt), depending on GC-content. They covered a 686 nt long part of the cyp1A1 mRNA (total length 1539 nt) between nucleotides 405 and 1091 without intervening gaps. This region was chosen to avoid regions with high homology to cyp3A4 (e.g. nt 325-363). One short homologous region could not be avoided and was therefore covered by an unlabelled oligonucleotide (see below).

The DO and CO were chosen so as not to be complementary to each other (DO and CO being complementary to each other would result in unspecific binding of DO to the beads via their direct binding to CO). 3 oligonucleotides had a too high degree of complementarity to others and were not labeled. These unlabeled oligonucleotides (UO) were nevertheless prepared and added to the hybridization solution to ensure that the respective part of the cyp1A1 mRNA was completely covered and thus in a double-stranded, more stable conformation. A fourth unlabelled oligonucleotide was prepared to cover a region with a high degree of homology to cyp3A4 (31 Cy1-UO).

The CO were chosen in a way that they were spaced relatively evenly between the DO. Furthermore, every DO was chosen to have the nucleotide A, C or T at the 5' terminus, because G is a known quencher of rhodamine-6G fluorescence.

In addition, a set of 20 FRET quencher oligonucleotides (FQO) was prepared. These were complementary to the 5' terminal part of the DO, however, they were only 15 nt long, resulting in a lower minimal melting temperature Tm of 38° C. They were labeled with a red oxazine dye at the 3' terminus. All oligonucleotides were synthesized according to standard procedures.

Stock solutions of oligonucleotides were prepared in TE-buffer (DEPC-treated water with 10 mM Tris-HCl, 1 mM EDTA pH 8.0) at a concentration of 100 µM and frozen at −80° C. DO-, CO-, UO- and FQO-mixtures were prepared (by adding equal amounts of each oligonucleotide solution) at a concentration of 100 µM. The concentration of each individual oligonucleotide in these mixtures was 5 µM for DO-mixture and FQO-mixture, 12.5 µM for CO-mixture and 25 µM for UO-mixture.

The following table 6 shows a complete list of all oligonucleotides used for the detection of cyp1A1 mRNA analyte. The position given below for the CO, DO and UO refers to the position on a strand complementary to the mRNA analyte.

TABLE 6

List of oligonucleotides used for the detection of cyp1A1 mRNA

| position | Name | sequence |
|---|---|---|
| 8 CO (capture oligonucleotides) comprising a linker of 15 T-nucleotides (T15) and biotin attached to 5' terminus | | |
| 505-525 | 1 Cy1-CO | Biotin-5'-T15-ctgcaacgtgcttatcaggac-3' |
| 526-544 | 2 Cy1-CO | Biotin-5'-T15-caggccctgccatcagctc-3' |
| 633-656 | 3 Cy1-CO | Biotin-5'-T15-ttgactaggctaagcagttcttgg-3' |
| 657-679 | 4 Cy1-CO | Biotin-5'-T15-cctccccgaaattattattcagg-3' |

TABLE 6-continued

List of oligonucleotides used for the detection of cyp1A1 mRNA

| position | Name | sequence |
|---|---|---|
| 745-766 | 5 Cy1-CO | Biotin-5'-T15-cattcaggtccttgaaggcatt-3' |
| 767-791 | 6 Cy1-CO | Biotin-5'-T15-ttctgcatgaagctgtagaacttct-3' |
| 987-1008 | 7 Cy1-CO | Biotin-5'-T15-gttcatcaccaaatacatgagg-3' |
| 1033-1055 | 8 Cy1-CO | Biotin-5'-T15-ccaatcactgtgtctagctcctc-3' |

20 DO (detection oligos) 5' labelled with rhodamine-6G (Rh6G)

| position | Name | sequence |
|---|---|---|
| 405-422 | 9 Cy1-DO | Rh6G-5'-ccattctgggccaggcgc-3' |
| 423-445 | 10 Cy1-DO | Rh6G-5'-aggcaatggagaaacttttcagg-3' |
| 446-463 | 11 Cy1-DO | Rh6G-5'-ttgaggaggctgggtcag-3' |
| 464-485 | 12 Cy1-DO | Rh6G-5'-tgctcttccaggtagcaggagg-3' |
| 570-592 | 13 Cy1-DO | Rh6G-5'-tgacattggtcactgataccacc-3' |
| 593-611 | 14 Cy1-DO | Rh6G-5'-ccaaagcaaatggcacaga-3' |
| 612-632 | 15 Cy1-DO | Rh6G-5'-tggttgtggtcatagcgccgg-3' |
| 680-699 | 16 Cy1-DO | Rh6G-5'-tgggtttccagagccaacca-3' |
| 700-722 | 17 Cy1-DO | Rh6G-5'-cgaagaatagggatgaactcagc-3' |
| 723-744 | 18 Cy1-DO | Rh6G-5'-cagggaagggttgggtaggtag-3' |
| 792-814 | 19 Cy1-DO | Rh6G-5'-ttttgtagtgctccttgaccatc-3' |
| 815-833 | 20 Cy1-DO | Rh6G-5'-atgtggcccttctcaaagg-3' |
| 834-856 | 21 Cy1-DO | Rh6G-5'-tcaggctgtctgtgatgtcccgg-3' |
| 867-878 | 22 Cy1-DO | Rh6G-5'-tgcttctcctgacagtgctcaa-3' |
| 879-898 | 23 Cy1-DO | Rh6G-5'-cattggcgttctcatccagc-3' |
| 899-922 | 24 Cy1-DO | Rh6G-5'-tgatcttctcatctgacagctgga-3' |
| 923-946 | 25 Cy1-DO | Rh6G-5'-caaagaggtccaagacgatgttaa-3' |
| 947-967 | 26 Cy1-DO | Rh6G-5'-tgactgtgtcaaacccagctc-3' |
| 1009-1032 | 27 Cy1-DO | Rh6G-5'-ttggatctttctctgtaccctggg-3' |
| 1070-1091 | 28 Cy1-DO | Rh6G-5'-tgggatctgtcagagagccggg-3' |

4 UO (unlabelled oligonucleotides)

| position | Name | sequence |
|---|---|---|
| 486-504 | 29 Cy1-UO | 5'-ctcagcctccttgctcaca-3' |
| 545-569 | 30 Cy1-UO | 5'-acatacctgtaggggttaaagtgcc-3' |
| 968-986 | 31 Cy1-UO | 5'-ctccaggagatagcagttg-3' |
| 1056-1069 | 32 Cy1-UO | 5'-gccgccgtgacctg-3' |

20 FQO (FRET quencher oligos) 3' labeled with red oxazine dye (RO)

| | Name | sequence |
|---|---|---|
| 9 Cy1-DO | 9 Cy1-FQO | 5'-cct ggc cca gaa tgg-3'-RO |
| 10 Cy1-DO | 10 Cy1-FQO | 5'-gtt tct caa ttg cct-3'-RO |
| 11 Cy1-DO | 11 Cy1-FQO | 5'-acc cag cct cct caa-3'-RO |
| 12 Cy1-DO | 12 Cy1-FQO | 5'-cta cct gga aga gca-3'-RO |
| 13 Cy1-DO | 13 Cy1-FQO | 5'-cag tga cca atg tca-3'-RO |
| 14 Cy1-DO | 14 Cy1-FQO | 5'-tgc cat ttg ctt tgg-3'-RO |
| 15 Cy1-DO | 15 Cy1-FQO | 5'-cta tga cca caa cca-3'-RO |

TABLE 6-continued

List of oligonucleotides used for the detection of cyp1A1 mRNA

| position | Name | sequence | | |
|---|---|---|---|---|
| 16 | Cy1-DO 16 | Cy1-FQO | 5'-ggc tct gga aac cca-3' | -RO |
| 17 | Cy1-DO 17 | Cy1-FQO | 5'-cat ccc tat tct tcg-3' | -RO |
| 18 | Cy1-DO 18 | Cy1-FQO | 5'-ccc aac cct tcc ctg-3' | -RO |
| 19 | Cy1-DO 19 | Cy1-FQO | 5'-agg agc act aca aaa-3' | -RO |
| 20 | Cy1-DO 20 | Cy1-FQO | 5'-tga gaa ggg cca cat-3' | -RO |
| 21 | Cy1-DO 21 | Cy1-FQO | 5'-tca cag aca gcc tga-3' | -RO |
| 22 | Cy1-DO 22 | Cy1-FQO | 5'-ctg tca gga gaa gca-3' | -RO |
| 23 | Cy1-DO 23 | Cy1-FQO | 5'-atg aga acg cca atg-3' | -RO |
| 24 | Cy1-DO 24 | Cy1-FQO | 5'-cag atg aga aga tca-3' | -RO |
| 25 | Cy1-DO 25 | Cy1-FQO | 5'-tct tgg acc tct ttg-3' | -RO |
| 26 | Cy1-DO 26 | Cy1-FQO | 5'-ggt ttg aca cag tca-3' | -RO |
| 27 | Cy1-DO 27 | Cy1-FQO | 5'-cag aga aag atc caa-3' | -RO |
| 28 | Cy1-DO 28 | Cy1-FQO | 5'-ctc tga cag atc cca-3' | -RO |

Expression of cyp1A1 mRNA in HepG2 Cells

For experiment the cells were seeded at $1*10^4$ cells/50 µl per well in three 384 titerplates (Greiner; catalogue number 781091) in DMEM-F12 supplemented with 10% FCS. After 24 h of incubation at 37° C. and 5% $CO_2$, 10 µl of 3-methyl-cholanthrene (3-MC) in different concentrations was added for stimulation of cyp1A1 expression for 24 h at 37° C. and 5% $CO_2$. The final 3-MC concentrations were 0 µM (control), 0 µM+0.02% DMSO (DMSO-control), 0.1 µM, 0.3 µM, 0.7 µM, 1 µM, 1.3 µM, 1.7 µM, 2 µM, 2.5 µM, 3 µM and 3.5 µM. On each plate each concentration was present 32 times.

3-MC stock solution was prepared with DMSO and diluted with DMEM-F12+10% FCS, the final DMSO concentration in the wells never exceeded 0.02%. After 24 h the stimulation mix was removed, 50 µl of lysis buffer were added to each well and incubation took place for 15 min at 37° C., 5% $CO_2$. Then the plate was frozen at −20° C. for three days until the assay procedure was performed.

Assay Procedure

24 µl of the cell lysate from each well of the cell culture plates was transferred to a well of one of the three glass bottom measurement plates (Nanocarrier™ 384/30, Evotec Technologies). A hybridization solution was prepared using the CO, DO and UO mixture solutions described above. Appropriate volumes were added to lysis buffer to yield a final concentration of 7 nM of each CO, DO and UO. Furthermore, the hybridization solution contained $3.7*10^3$ SA beads/ml.

To each well, 1 µl of hybridization solution was added resulting in a final concentration of 0.28 nM of each DO, CO and UO. The final SA bead number per well was 3700. The measurement plate was placed into a humid incubator and incubated over night (for approximately 17 h) at 53° C.

The next day a quencher solution was prepared using the FQO mixture solution and the stock solution of biotinylated red oxazine dye described above. Appropriate volumes were added to lysis buffer to yield a final concentration of 72.8 nM of each FQO and a final concentration of 1.3 µM of the biotinylated red oxazine dye. 1 µl of the quencher solution was added to each well of the measurement plate, resulting in a final concentration of 2.8 nM for each FQO and 50 nM of the biotinylated red oxazine dye. The measurement plate was again placed into a humid incubator and incubated for 1 h at 35° C. Then the plate was measured as described above.

Result

The result is depicted in FIG. 9. With increasing 3-MC concentration (used to stimulate expression of cyp1A1 mRNA) an increase in the average fluorescence intensity/bead pixel stemming from the detection oligonucleotide—mRNA analyte—capture oligonucleotide complex bound to beads can be observed. The $EC_{50}$ determined for each plate was 0.8 µM with a standard deviation of 0.05 µM between the three plates. Thus, the results show an excellent reproducibility although the absolute values of the three plates differ. This result is similar to published results, (see e.g Delescluse, C., Ledirac, N., de Sousa, G., Pralavorio, M., Botta-Fridlund, D., Letreut, Y., and Rahmani, R. (1997), Comparative study of Cyp1A1 induction by 3-methylcholanthrene in various human hepatic and epidermal cell types. Toxicology in Vitro 11, 443-450). From a Northern Blot in this publication an $EC_{50}$ of ~0.5 µM can be roughly estimated, this is in excellent agreement with the present results.

EXAMPLE 3

Influence of the Use of the Reference Emission of the Biotinylated Second Dye on Assay Sensitivity This example is based on the images obtained according to example 1a and relates to FIGS. 10 and 11. In a first instance, image analysis was conducted utilizing the emission of the reporter labeling the beads (see reference images). In a second instance, image analysis was performed without making use of such reference images and relied solely on the emission of the reporter labeling the detection oligonucleotides bound to the beads via the analyte-CO-complex. The sensitivity of the assay is significantly reduced by at least one order of magnitude if one relies only on the emission of the reporter labeling the detection oligonucleotides bound to the beads via the analyte-CO-complex (see FIG. 10). Bead recognition utilizing a reporter labeling the bead (second reporter) is advantageous because otherwise contaminations of the sample or sufficiently large aggregates of DO would be recognized erroneously as signal stemming from the first reporter of the detection oligonucleotide-analyte-complex.

EXAMPLE 4

Influence of the Addition of FQO on Assay Sensitivity

Assay Procedure

The assay was in essence conducted as described in example 1a above. However, nine (instead of eight) c-fos RNA dilutions were prepared, see table 7 below. Furthermore eight (instead of four) 24 μl samples of each concentration were added to the wells of the measurement plate (Nanocarrier™ 96/30, Evotec Technologies). In contrast to example 1a only to four wells of each concentration the usual quencher solution (containing FQO and biotinlyated red oxazine dye) was added. To the other four wells, a modified solution without FQO was added, containing only the biotinlyated red oxazine dye.

TABLE 7

| RNA copy number/well c-fos | |
|---|---|
| copy number/24 μl (= copy number/well) | final RNA concentration |
| $1 * 10^9$ | 69 pM |
| $1 * 10^8$ | 6.9 pM |
| $1 * 10^7$ | 692 fM |
| $5 * 10^6$ | 346 fM |
| $2.5 * 10^6$ | 173 fM |
| $1 * 10^6$ | 69 fM |
| $5 * 10^5$ | 34.6 fM |
| $2.5 * 10^5$ | 17.3 fM |
| $1 * 10^5$ | 6.9 fM |

Result

The specific quenching of free DO via the hybridization of FQO to these DO significantly reduces the fluorescence intensity of the background to ~25% of the values without FQO: 116 intensity counts/background pixel as opposed to 444 intensity counts/background pixel without FQO. The strategy proposed by the present invention therefore improves significantly the sensitivity of the assay (in the present example by approximately one order of magnitude). This becomes visible in FIG. 12. In contrast to the image analysis described in general above, no background signal intensity was determined in the vicinity of the beads and subtracted from the signal intensity detected per bead pixel. This procedure was chosen to demonstrate the influence of utilizing FQOs according to the present invention.

---

The invention claimed is:

1. A method for detecting an analyte in a sample comprising, in a homogeneous format, the steps of
providing detection probes labeled with a first reporter, which detection probes are capable of binding to the analyte,
providing a solid support labeled with a second reporter different than the first reporter,
providing capture probes bound or capable of binding to the solid support, which capture probes are capable of binding to the analyte, thus concentrating the analyte on the solid support,
contacting the sample with the detection probes, the solid support and the capture probes, and
detecting the detection probes, wherein
the detection comprises recording an image of the sample at an emission wavelength of the second reporter simultaneously with an image used for detecting the detection probes, generating a mask obtained from imaging the sample at the emission wavelength of the second reporter and applying this mask to the image of the sample used for detecting the detection probes.

2. The method according to claim 1 wherein the detection probes are detection oligonucleotides and the capture probes are capture oligonucleotides.

3. The method according to claim 2 wherein the capture oligonucleotides are covalently bound to the solid support.

4. The method according to claim 2 wherein the capture oligonucleotides are capable of binding to the solid support via affinity interaction.

5. The method according to claim 4 wherein the capture oligonucleotides comprise a first affinity unit capable of binding to a second affinity unit attached to the solid support.

6. The method according to claim 5 wherein the first affinity unit is biotin and the second affinity unit is streptavidin or avidin.

7. The method according to claim 5 wherein the capture oligonucleotides comprise a linker sequence, linking the sequence of the capture oligonucleotide complementary to the analyte with the first or second affinity unit or the solid support.

8. The method according to claim 2 wherein at least two different analytes are detected by providing at least two different sets of detection oligonucleotides and at least two different sets of capture oligonucleotides.

9. The method according to claim 8 wherein the different sets of detection oligonucleotides are labeled with different reporters.

10. The method according to claim 8 wherein the reporters of one set are identical, have the same excitation wavelength and/or the same emission wavelength.

11. The method according to claim 8 wherein the capture oligonucleotides of different sets are attached or capable of binding to different solid supports.

12. The method according to claim 11 wherein the solid supports differ in the affinity units attached thereto, which affinity units interact with affinity units of the capture oligonucleotides.

13. The method according to claim 2 wherein the first reporter labeling the detection oligonucleotides differs in its excitation wavelength and/or its emission wavelength from the second reporter labeling the solid support.

14. The method according to claim 13 wherein the difference in the excitation wavelength and/or emission wavelength between first and second reporter is at least 10 nm.

15. The method according to claim 2 wherein the image recorded at the emission wavelength of the second reporter is corrected such that it spatially matches with the image used for detecting the detection oligonucleotides, or vice versa.

16. The method according to claim 2 wherein the image of the sample used for detecting the detection oligonucleotides is acquired at the emission wavelength of the first reporter.

17. The method according to claim 1 wherein the first and/or second reporter is luminescent.

18. The method according to claim 1 wherein the first and/or second reporter is a dye.

19. The method according to claim 1 wherein the solid support is a bead, a cell, a pollen, or a plurality thereof.

20. The method according to claim 1 further comprising the step of quantifying the analyte.

21. The method according to claim 20 wherein the detection probes are detection oligonucleotides and wherein the quantification is performed by determining an amount of detection oligonucleotides bound to the analyte.

22. The method according to claim 20 wherein the detection probes are detection oligonucleotides and wherein the amount of detection oligonucleotides bound to the analyte is expressed as the emission intensity emitted by the first reporter.

23. The method according to claim 20 wherein the detection probes are detection oligonucleotides and further comprising the step of determining an intensity of a background emission in the vicinity of the solid support and considering such intensity when determining the amount of detection oligonucleotides.

24. The method according to claim 1 wherein the detection probes are aptameres, oligonucleotides, or antibodies.

25. The method according to claim 1 wherein the analyte is a protein or a nucleic acid.

26. The method according to claim 1 wherein the sample is a cell or an in vitro prepared sample.

27. The method according to claim 1 further comprising adding a substance to a cellular sample and analyzing whether the substance induces, inhibits, or modulates generation of the analyte.

28. The method according to claim 1 further comprising adding a substance to a cellular sample and analyzing the substance for pharmaceutical activity, for diagnosis, or for side effects.

29. The method of claim 1 wherein the detection is conducted in the presence of quenching probes binding to surplus detection probes not bound to the analyte and thereby quenching at least partially an emission of the first reporter of the surplus detection probes.

30. The method according to claim 29 wherein the detection probes are detection oligonucleotides, the capture probes are capture oligonucleotides, and the quenching probes are quenching oligonucleotides.

31. The method according to claim 30 wherein the detection oligonucleotides are labeled with a first fluorescent dye and/or the solid support is labeled with a second fluorescent dye.

32. The method according to claim 31 wherein a melting temperature of a hybrid between detection oligonucleotides and analyte is at least 1° C. higher than a melting temperature of a hybrid between detection oligonucleotides and quenching oligonucleotides under test conditions.

33. The method according to claim 30 wherein a hybrid between detection oligonucleotides and analyte has a higher melting temperature than a hybrid between detection oligonucleotides and quenching oligonucleotides.

34. The method according to claim 30 wherein contacting the sample with the detection oligonucleotides is performed under first hybridization conditions allowing the generation of a stable hybrid between detection oligonucleotides and analyte.

35. The method according to claim 34 wherein contacting the sample with the quenching oligonucleotides is performed under second hybridization conditions allowing the generation of a stable hybrid between surplus detection oligonucleotides not bound to the analyte and quenching oligonucleotides.

36. The method according to claim 35 wherein the second hybridization conditions do not destabilize a hybrid between detection oligonucleotides and analyte formed under the first hybridization conditions.

37. The method according to claim 30 wherein the capture oligonucleotides are covalently bound to the solid support.

38. The method according to claim 30 wherein the capture oligonucleotides are capable of binding to the solid support via affinity interaction.

39. The method according to claim 38 wherein the capture oligonucleotides comprise a first affinity unit capable of binding to a second affinity unit attached to the solid support.

40. The method according to claim 39 wherein the first affinity unit is biotin and the second affinity unit is streptavidin or avidin.

41. The method according to claim 39 wherein the capture oligonucleotides comprise a linker sequence, linking the sequence of the capture oligonucleotide complementary to the analyte with the first or second affinity unit or the solid support.

42. The method according to claim 30 wherein the detection oligonucleotides comprise a linker sequence, linking the sequence of detection oligonucleotide complementary to the analyte with the first reporter.

43. The method according to claim 30 wherein at least two different analytes are detected by providing at least two different sets of detection oligonucleotides and at least two different sets of capture oligonucleotides.

44. The method according to claim 43 wherein the different sets of detection oligonucleotides are labeled with different reporters.

45. The method according to claim 43 wherein the reporters of one set are identical, have the same excitation wavelength and/or the same emission wavelength.

46. The method according to claim 43 wherein the capture oligonucleotides of different sets are attached or capable of binding to different solid supports.

47. The method according to claim 46 wherein the solid supports differ in the affinity units attached thereto, which affinity units interact with affinity units of the capture oligonucleotides.

48. The method according to claim 30 wherein the quenching oligonucleotides have a quenching unit.

49. The method according to claim 48 wherein the first reporter is a donor of a Förster resonance energy transfer (FRET) donor-acceptor-pair and the quenching unit is an acceptor of the donor-acceptor-pair.

50. The method according to claim 48 wherein the quenching unit is a dark quencher which quenches at least partially the emission of the first reporter by dissipating an energy of an excited state of the first reporter into the environment.

51. The method according to claim 29 wherein the solid support is a bead, a cell, a pollen, or a plurality thereof.

52. The method according to claim 29 further comprising the step of quantifying the analyte.

53. The method according to claim 52 wherein the detection probes are detection oligonucleotides and wherein the quantification is performed by determining an amount of detection oligonucleotides bound to the analyte.

54. The method according to claim 52 wherein the detection probes are detection oligonucleotides and wherein the amount of detection oligonucleotides bound to the analyte is expressed as the emission intensity emitted by the first reporter.

55. The method according to claim 52 wherein the detection probes are detection oligonucleotides and further comprising the step of determining an intensity of a background emission in the vicinity of the solid support and considering such intensity when determining the amount of detection oligonucleotides.

56. The method according to claim 29 wherein the detection probes are aptameres, oligonucleotides, or antibodies.

57. The method according to claim 29 wherein the analyte is a protein or a nucleic acid.

58. The method according to claim 29 wherein the sample is a cell or an in vitro prepared sample.

59. The method according to claim 29 further comprising adding a substance to a cellular sample and analyzing whether the substance induces, inhibits, or modulates generation of the analyte.

60. The method according to claim 29 further comprising adding a substance to a cellular sample and analyzing the substance for pharmaceutical activity, for diagnosis, or for side effects.

* * * * *

SEQUENCE LISTING

<160> NUMBER OF SEQ ID NOS: 107

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA
<220> FEATURE:
<221> NAME/KEY: misc_binding
<222> LOCATION: (1)

<400> SEQUENCE: 1
ggctctggtc tgcgatggg                                                  19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA
<220> FEATURE:
<221> NAME/KEY: misc_binding
<222> LOCATION: (1)

<400> SEQUENCE: 2
gggactccga aagggtgagg                                                 20

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA

```
<220> FEATURE:
<221> NAME/KEY: misc_binding
<222> LOCATION: (1)

<400> SEQUENCE: 3 cctttctctct tcttcttctg gagataa                                      27

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA
<220> FEATURE:
<221> NAME/KEY: misc_binding
<222> LOCATION: (1)

<400> SEQUENCE: 4
attcctttcc cttcggattc t                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA
<220> FEATURE:
<221> NAME/KEY: misc_binding
<222> LOCATION: (1)

<400> SEQUENCE: 5
atctcggtct gcaaagcaga c                                             21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA
<220> FEATURE:
<221> NAME/KEY: misc_binding
<222> LOCATION: (1)

<400> SEQUENCE: 6
tctccttcag caggttggca                                               20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA
<220> FEATURE:
<221> NAME/KEY: misc_binding
<222> LOCATION: (1)

<400> SEQUENCE: 7
ccacagacat ctcttctggg aag                                           23

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:capture
      oligonuecleotide for the c-fos mRNA
```

```
-continued

<220> FEATURE:
<221> NAME/KEY: misc_binding
<222> LOCATION: (1)

<400> SEQUENCE: 8
ccccagtcag atcaagggaa g                                              21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 9
atgaagttgg cactggagac gg                                             22

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 10
atggcagtga ccgtggga                                                  18

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 11
caggtccgga ctggtcgag                                                 19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 12
cgggctgcac cagccactg                                                 19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
```

-continued

```
<220> FEATURE:
<221> NAME/KEY: misc_binding
<222> LOCATION: (1)

<400> SEQUENCE: 13
ccagccctgg agtaagcc                                                       18

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 14
ctcctgtcat ggtcttcaca acg                                                 23

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 15
ccaatgctct gcgctcggc                                                      19

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 16
ctgttccacc ttgcccctcc tg                                                  22

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 17
ccctcctccg gttgcgg                                                        17

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
```

```
<220> FEATURE:
<221> NAME/KEY: misc_binding
<222> LOCATION: (1)

<400> SEQUENCE: 18
cgcttggagt gtatcagtca gct                                          23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 19
ccaggatgaa ctctagtttt tcct                                         24

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 20
caggcaggtc ggtgagctg                                               19

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 21
cccaggtcat cagggatctt g                                            21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 22
aggcctcctc agactccggg                                              20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
```

```
<220> FEATURE:
<221> NAME/KEY: misc_binding
<222> LOCATION: (1)

<400> SEQUENCE: 23
tgaggagagg cagggtga                                                18

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 24
agggcttggg ctcagggtca t                                            21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 25
tgctcttgac aggttccact g                                            21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 26
aagtcatcaa agggctcggt                                              20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the c-fos mRNA
<220> FEATURE:
<221> NAME/KEY: misc_binding
<222> LOCATION: (1)

<400> SEQUENCE: 27
cctggatgat gctgggaaca gg                                           22

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:unlabeled
      oligonucleotide for the c-fos mRNA
```

<400> SEQUENCE: 28
gccacagagg agacgaggg					19

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence:unlabeled
      oligonucleotide for the c-fos mRNA

<400> SEQUENCE: 29
ccagcggagg gggcg					15

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:unlabeled
      oligonucleotide for the c-fos mRNA

<400> SEQUENCE: 30
catttggctg cagccatctt					20

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:unlabeled
      oligonucleotide for the c-fos mRNA

<400> SEQUENCE: 31
ttctcatctt ctagttggtc tgtctc					26

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence:unlabeled
      oligonucleotide for the c-fos mRNA

<400> SEQUENCE: 32
gtggcaacct ctggcaggc					19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:unlabeled
      oligonucleotide for the c-fos mRNA

<400> SEQUENCE: 33
cttcagctcc atgctgctga					20

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:

```
<221> NAME/KEY: misc_binding
<222> LOCATION: (15)

<400> SEQUENCE: 34
cagtgccaac ttcat                                                    15

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 35
cacggtcact gccat                                                    15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 36
accagtccgg acctg                                                    15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 37
ggctggtgca gcccg                                                    15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 38
ttactccagg gctgg                                                    15

<210> SEQ ID NO 39
<211> LENGTH: 15
<212> TYPE: DNA
<213> ORGANISM: Artificial Sequence
```

```
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 39
agaccatgac aggag                                                    15

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 40
agcgcagagc attgg                                                    15

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 41
ggcaaggtgg aacag                                                    15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 42
gcaaccggag gaggg                                                    15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 43
gatacactcc aagcg                                                    15
```

```
<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 44
tagagttcat cctgg                                                        15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 45
tcaccgacct gcctg                                                        15

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 46
ccctgatgac ctggg                                                        15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 47
agtctgagga ggcct                                                        15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)
```

<400> SEQUENCE: 48
ccctgcctct cctca                                                      15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 49
ctgagcccaa gccct                                                      15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 50
aacctgtcaa gagca                                                      15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 51
gccctttgat gactt                                                      15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 52
ccagcatcat ccagg                                                      15

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence:forward -continued primer for the c-fos mRNA

<400> SEQUENCE: 53
gcgaattcct cgggcttcaa cgcaga                        26

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:reverse
      primer for the c-fos mRNA

<400> SEQUENCE: 54
atggatccca gcgtgggtga gctga                         25

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 55
ctgcaacgtg cttatcagga c                             21

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 56
caggccctgc catcagctc                                19

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 57
ttgactaggc taagcagttc ttgg                          24

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 58

```
cctccccgaa attattattc agg                                             23

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 59
cattcaggtc cttgaaggca tt                                              22

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 60
ttctgcatga agctgtagaa cttct                                           25

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 61
gttcatcacc aaatacatga gg                                              22

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence:capture
      oligonucleotide for the cyp 1A1 mRNA
<220> FEATURE:
<221> NAME/KEY: misc_binding
<222> LOCATION: (1)

<400> SEQUENCE: 62
ccaatcactg tgtctagctc ctc                                             23

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 63
```

```
ccattctggg ccaggcgc                                                       18

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 64
aggcaatgga gaaactttc agg                                                  23

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 65
ttgaggaggc tgggtcag                                                       18

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 66
tgctcttcca ggtagcagga gg                                                  22

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 67
tgacattggt cactgatacc acc                                                 23

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 68
```

```
ccaaagcaaa tggcacaga                                                19
```

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 69

```
tggttgtggt catagcgccg g                                             21
```

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 70

```
tgggtttcca gagccaacca                                               20
```

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 71

```
cgaagaatag ggatgaactc agc                                           23
```

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 72

```
cagggaaggg ttgggtaggt ag                                            22
```

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 73
ttttgtagtg ctccttgacc atc                    23

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 74
atgtggccct tctcaaagg                         19

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 75
tcaggctgtc tgtgatgtcc cgg                    23

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 76
tgcttctcct gacagtgctc aa                     22

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 77
cattggcgtt ctcatccagc                        20

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 78

```
tgatcttctc atctgacagc tgga                                          24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 79
caaagaggtc caagacgatg ttaa                                          24

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 80
tgactgtgtc aaacccagct c                                             21

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 81
ttggatcttt ctctgtaccc tggg                                          24

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the cyp 1A1 mRNA
<220> FEATURE:
<221> NAME/KEY: misc_binding
<222> LOCATION: (1)

<400> SEQUENCE: 82
tgggatctgt cagagagccg gg                                            22

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence:unlabelled
      oligonucleotide for the cyp 1A1 mRNA

<400> SEQUENCE: 83
ctcagcctcc ttgctcaca                                                19
```

```
<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence:unlabelled
      oligonucleotide for the cyp 1A1 mRNA

<400> SEQUENCE: 84
acatacctgt aggggttaaa gtgcc                                           25

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence:unlabelled
      oligonucleotide for the cyp 1A1 mRNA

<400> SEQUENCE: 85
ctccaggaga tagcagttg                                                  19

<210> SEQ ID NO 86
<211> LENGTH: 14
<212> TYPE: DNA
<213> ORGANISM: Artificial Sequence
<220> FEATURE:
<223> OTHER INFORMATION: Description of Artificial Sequence:unlabelled
      oligonucleotide for the cyp 1A1 mRNA

<400> SEQUENCE: 86
gccgccgtga cctg                                                       14

<210> SEQ ID NO 87
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 87
cctggcccag aatgg                                                      15

<210> SEQ ID NO 88
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 88
gtttctccat tgcct                                                      15

<210> SEQ ID NO 89
<211> LENGTH: 15
<212> TYPE: DNA
<213> ORGANISM: Artificial Sequence
<220> FEATURE:
<223> OTHER INFORMATION: Description of Artificial Sequence:FRET
```

```
          quencher oligonucleotide for the respective detection
          oligonucleotide
<220> FEATURE:
<221> NAME/KEY: misc_binding
<222> LOCATION: (15)

<400> SEQUENCE: 89
acccagcctc ctcaa                                                    15

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 90
ctacctggaa gagca                                                    15

<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 91
cagtgaccaa tgtca                                                    15

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 92
tgccatttgc tttgg                                                    15

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 93
ctatgaccac aacca                                                    15

<210> SEQ ID NO 94
```

```
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 94
ggctctggaa accca                                                      15

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 95
catccctatt cttcg                                                      15

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 96 cccaacccctt ccctg                                                     15

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 97
aggagcacta caaaa                                                      15

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 98
```

```
tgagaagggc cacat                                              15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 99
tcacagacag cctga                                              15

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 100
ctgtcaggag aagca                                              15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 101
atgagaacgc caatg                                              15

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 102
cagatgagaa gatca                                              15

<210> SEQ ID NO 103
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
```

```
<220> FEATURE:
<221> NAME/KEY: misc_binding
<222> LOCATION: (15)

<400> SEQUENCE: 103
tcttggacct ctttg                                                        15

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 104
ggtttgacac agtca                                                        15

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 105
cagagaaaga tccaa                                                        15

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the respective detection
      oligonucleotide
<220> FEATURE:
<221> NAME/KEY: misc_binding
<222> LOCATION: (15)

<400> SEQUENCE: 106
ctctgacaga tccca                                                        15

<210> SEQ ID NO 107
<211> LENGTH: 81
<212> TYPE: DNA
<213> ORGANISM: Homo sapiens

<400> SEQUENCE: 107
accgagattg ccaacctgct gaaggagaag gaaaaactag agttcatcct                  50
ggcagctcac cgacctgcct gcaagatccc t                                      81
```